(12) United States Patent
Lockett et al.

(10) Patent No.: US 10,658,679 B2
(45) Date of Patent: *May 19, 2020

(54) PRINTED ENERGY STORAGE DEVICE

(71) Applicant: Printed Energy Pty Ltd, Brisbane, Queensland (AU)

(72) Inventors: Vera N. Lockett, Phoenix, AZ (US); John G. Gustafson, Chandler, AZ (US); Alexandra E. Hartman, Tolleson, AZ (US); Mark D. Lowenthal, Gilbert, AZ (US); William J. Ray, Fountain Hills, AZ (US)

(73) Assignee: Printed Energy Pty Ltd, Brisbane, Queensland (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/986,423

(22) Filed: May 22, 2018

(65) Prior Publication Data

US 2018/0269494 A1 Sep. 20, 2018

Related U.S. Application Data

(63) Continuation of application No. 15/374,699, filed on Dec. 9, 2016, now Pat. No. 10,020,516, which is a
(Continued)

(51) Int. Cl.
*H01M 6/40* (2006.01)
*C07D 233/58* (2006.01)
(Continued)

(52) U.S. Cl.
CPC ............ *H01M 6/40* (2013.01); *C07D 233/58* (2013.01); *H01M 2/145* (2013.01); *H01M 2/166* (2013.01);
(Continued)

(58) Field of Classification Search
CPC ........ H01M 6/40; H01M 6/164; H01M 6/066; H01M 6/06; H01M 4/12; H01M 4/42;
(Continued)

(56) References Cited

U.S. PATENT DOCUMENTS

| | | |
|---|---|---|
| 2,912,479 A | 11/1959 | Poole |
| 4,312,931 A | 1/1982 | Witherspoon et al. |

(Continued)

FOREIGN PATENT DOCUMENTS

| | | |
|---|---|---|
| CN | 1391705 | 1/2003 |
| CN | 1427494 | 7/2003 |

(Continued)

OTHER PUBLICATIONS

International Search Report and Written Opinion in PCT Application No. PCT/US2013/050949, dated Nov. 12, 2013, in 13 pages.
(Continued)

*Primary Examiner* — Jane J Rhee
(74) *Attorney, Agent, or Firm* — Knobbe Martens Olson & Bear, LLP

(57) ABSTRACT

A printed energy storage device includes a first electrode including zinc, a second electrode including manganese dioxide, and a separator between the first electrode and the second electrode, the first electrode, second, electrode, and separator printed onto a substrate. The device may include a first current collector and/or a second current collector printed onto the substrate. The energy storage device may include a printed intermediate layer between the separator and the first electrode. The first electrode, and the second electrode may include 1-ethyl-3-methylimidazolium tetrafluoroborate ($C_2mimBF_4$). The first electrode and the second electrode may include an electrolyte having zinc tetrafluoroborate ($ZnBF_4$) and 1-ethyl-3-methylimidazolium tetrafluoroborate ($C_2mimBF_4$). The first electrode, the second
(Continued)

electrode, the first current collector, and/or the second current collector can include carbon nanotubes. The separator may include solid microspheres.

20 Claims, 6 Drawing Sheets

Related U.S. Application Data continuation of application No. 14/050,145, filed on Oct. 9, 2013, now Pat. No. 9,520,598.

(60) Provisional application No. 61/712,219, filed on Oct. 10, 2012.

(51) Int. Cl.

| | | |
|---|---|---|
| *H01M 4/62* | (2006.01) | |
| *H01M 4/06* | (2006.01) | |
| *H01M 2/14* | (2006.01) | |
| *H01M 2/16* | (2006.01) | |
| *H01M 6/16* | (2006.01) | |
| *H01M 4/38* | (2006.01) | |
| *H01M 4/50* | (2010.01) | |
| H01G 11/30 | (2013.01) | |
| H01G 11/36 | (2013.01) | |

(52) U.S. Cl.
CPC ........... *H01M 2/1653* (2013.01); *H01M 4/06* (2013.01); *H01M 4/38* (2013.01); *H01M 4/502* (2013.01); *H01M 4/622* (2013.01); *H01M 4/625* (2013.01); *H01M 6/164* (2013.01); *H01M 6/166* (2013.01); *H01G 11/30* (2013.01); *H01G 11/36* (2013.01); *H01M 2220/30* (2013.01); *H01M 2300/0045* (2013.01); *H01M 2300/0085* (2013.01)

(58) Field of Classification Search
CPC ........ H01M 4/50; H01M 4/625; H01M 4/661; H01M 4/663; H01M 4/666; H01M 4/668; H01M 10/0569; H01M 2220/30
See application file for complete search history.

(56) References Cited

U.S. PATENT DOCUMENTS

| | | |
|---|---|---|
| 4,760,494 A | 7/1988 | Crum |
| 5,116,701 A | 5/1992 | Kalisz |
| 5,573,868 A | 11/1996 | Umemoto et al. |
| 5,627,269 A | 5/1997 | Herak et al. |
| 5,948,464 A | 9/1999 | Delnick |
| 6,080,283 A | 6/2000 | Ray |
| 6,124,059 A | 9/2000 | Bohnstedt et al. |
| 6,242,129 B1 | 6/2001 | Johnson |
| 6,379,835 B1 | 4/2002 | Kucherovsky et al. |
| 6,475,670 B1 | 11/2002 | Ito |
| 6,527,955 B1 | 3/2003 | Sun |
| 6,641,908 B1 | 11/2003 | Clough |
| 6,728,096 B1 | 4/2004 | Smith et al. |
| 6,828,062 B2 | 12/2004 | Lu et al. |
| 7,067,104 B2 | 6/2006 | Sandhage |
| 7,112,389 B1 | 9/2006 | Arora et al. |
| 7,348,096 B2 | 3/2008 | Schubert et al. |
| 7,615,206 B2 | 11/2009 | Sandhage et al. |
| 7,727,290 B2 | 6/2010 | Zhang et al. |
| 8,029,927 B2 | 10/2011 | Tucholski |
| 8,119,273 B1 | 2/2012 | Gerald, II et al. |
| 8,119,278 B2 | 2/2012 | Bailey et al. |
| 8,460,823 B1 | 6/2013 | Delnick |
| 8,809,126 B2 | 8/2014 | Lowenthal et al. |
| 9,083,010 B2 | 7/2015 | Lockett et al. |
| 9,136,065 B2 | 9/2015 | Lockett et al. |
| 9,397,341 B2 | 7/2016 | Lockett et al. |
| 9,520,598 B2 | 12/2016 | Lockett et al. |
| 9,548,511 B2 | 1/2017 | Lockett et al. |
| 9,786,926 B2 | 10/2017 | Lockett et al. |
| 9,825,305 B2 | 11/2017 | Lockett et al. |
| 9,834,447 B2 | 12/2017 | Lockett et al. |
| 9,917,309 B2 | 3/2018 | Lockett et al. |
| 10,020,516 B2 | 7/2018 | Lockett et al. |
| 10,109,864 B2 | 10/2018 | Lockett et al. |
| 10,221,071 B2 | 3/2019 | Lockett et al. |
| 10,396,365 B2 | 8/2019 | Lockett et al. |
| 2001/0009734 A1 | 7/2001 | Clough |
| 2002/0071915 A1 | 6/2002 | Schubert et al. |
| 2002/0102465 A1 | 8/2002 | Chen et al. |
| 2002/0164530 A1 | 11/2002 | Iwakura et al. |
| 2003/0027051 A1 | 2/2003 | Kejha et al. |
| 2003/0099884 A1 | 5/2003 | Chiang et al. |
| 2003/0113624 A1 | 6/2003 | Kim et al. |
| 2003/0165744 A1 | 9/2003 | Schubert et al. |
| 2004/0023110 A1 | 2/2004 | Parent et al. |
| 2004/0151837 A1 | 8/2004 | Morita et al. |
| 2004/0191617 A1 | 9/2004 | Visco et al. |
| 2004/0221446 A1 | 11/2004 | Ohhara et al. |
| 2005/0058875 A1 | 3/2005 | Jerome |
| 2005/0175894 A1 | 8/2005 | Visco et al. |
| 2006/0177739 A1 | 8/2006 | Endo et al. |
| 2006/0216584 A1 | 9/2006 | Cheiky |
| 2006/0246355 A1 | 11/2006 | Min et al. |
| 2007/0128707 A1 | 6/2007 | Rorrer et al. |
| 2007/0212615 A1 | 9/2007 | Jost et al. |
| 2007/0281854 A1 | 12/2007 | Harbour et al. |
| 2008/0020284 A1 | 1/2008 | Michot et al. |
| 2008/0038170 A1 | 2/2008 | Sandhage et al. |
| 2008/0063931 A1 | 3/2008 | Zucker |
| 2008/0209876 A1 | 9/2008 | Miller |
| 2009/0075167 A1 | 3/2009 | Traulsen et al. |
| 2009/0130565 A1 | 5/2009 | Matsui et al. |
| 2009/0191460 A1 | 7/2009 | Fujiwara et al. |
| 2009/0246625 A1 | 10/2009 | Lu |
| 2009/0272946 A1 | 11/2009 | Le |
| 2010/0000441 A1 | 1/2010 | Jang et al. |
| 2010/0009255 A1 | 1/2010 | Hawkins et al. |
| 2010/0075222 A1 | 3/2010 | Watanabe |
| 2010/0183523 A1 | 7/2010 | Wagner |
| 2010/0203362 A1 | 8/2010 | Lam et al. |
| 2010/0233569 A1 | 9/2010 | Ono et al. |
| 2010/0284123 A1 | 11/2010 | Pulugurtha et al. |
| 2010/0285375 A1 | 11/2010 | Friesen et al. |
| 2011/0043037 A1 | 2/2011 | McIlroy et al. |
| 2011/0043968 A1 | 2/2011 | Kim et al. |
| 2011/0045337 A1 | 2/2011 | Lee et al. |
| 2011/0058309 A1 | 3/2011 | Eguchi et al. |
| 2011/0059361 A1 | 3/2011 | Wilkening et al. |
| 2011/0068296 A1 | 3/2011 | Huang et al. |
| 2011/0111283 A1 | 5/2011 | Rust, III et al. |
| 2011/0134585 A1 | 6/2011 | Shen et al. |
| 2011/0261502 A1* | 10/2011 | Gruner .................. H01G 11/02 361/502 |
| 2011/0281184 A1 | 11/2011 | Friesen et al. |
| 2011/0311857 A1 | 12/2011 | Tucholski |
| 2012/0014037 A1 | 1/2012 | Mastro et al. |
| 2012/0021457 A1 | 1/2012 | Tang |
| 2012/0028134 A1 | 2/2012 | Kim et al. |
| 2012/0100402 A1 | 4/2012 | Nesper et al. |
| 2012/0107666 A1 | 5/2012 | Bailey et al. |
| 2012/0161195 A1 | 6/2012 | Lowenthal et al. |
| 2012/0187906 A1 | 7/2012 | Martiensssen et al. |
| 2012/0241073 A1 | 9/2012 | Wiest et al. |
| 2012/0250225 A1 | 10/2012 | Aria et al. |
| 2012/0264034 A1 | 10/2012 | Waki et al. |
| 2013/0052509 A1 | 2/2013 | Halalay et al. |
| 2013/0089769 A1 | 4/2013 | Proctor et al. |
| 2013/0280579 A1 | 10/2013 | Wright et al. |
| 2013/0308248 A1 | 11/2013 | Leddy et al. |
| 2014/0002788 A1 | 1/2014 | Otts et al. |
| 2014/0014403 A1 | 1/2014 | Miller et al. |
| 2014/0017557 A1 | 1/2014 | Lockett et al. |
| 2014/0017558 A1 | 1/2014 | Lockett et al. |
| 2014/0017571 A1 | 1/2014 | Lockett et al. |

(56) References Cited

U.S. PATENT DOCUMENTS

| | | | |
|---|---|---|---|
| 2014/0029161 | A1 | 1/2014 | Beidaghi et al. |
| 2014/0072886 | A1 | 3/2014 | Urban et al. |
| 2014/0099528 | A1 | 4/2014 | Lockett et al. |
| 2014/0302373 | A1 | 10/2014 | Lockett et al. |
| 2015/0024247 | A1 | 1/2015 | Lockett et al. |
| 2015/0338403 | A1 | 11/2015 | Wang |
| 2016/0002054 | A1 | 1/2016 | Lockett et al. |
| 2016/0031843 | A1 | 2/2016 | Socha et al. |
| 2016/0322648 | A1 | 11/2016 | Lockett et al. |
| 2017/0125823 | A1 | 5/2017 | Lockett et al. |
| 2017/0222232 | A1 | 8/2017 | Lockett et al. |
| 2017/0309411 | A1 | 10/2017 | Qian et al. |
| 2018/0034067 | A1 | 2/2018 | Lockett et al. |
| 2018/0057363 | A1 | 3/2018 | Lockett et al. |
| 2018/0069246 | A1 | 3/2018 | Lockett et al. |
| 2018/0198136 | A1 | 7/2018 | Lockett et al. |
| 2018/0212253 | A1 | 7/2018 | Lockett et al. |
| 2019/0051909 | A1 | 2/2019 | Lockett et al. |
| 2019/0185329 | A1 | 6/2019 | Lockett et al. |
| 2019/0363370 | A1 | 11/2019 | Lockett et al. |

FOREIGN PATENT DOCUMENTS

| | | |
|---|---|---|
| CN | 1973397 | 5/2007 |
| CN | 101960546 | 1/2011 |
| CN | 102007070 | 4/2011 |
| CN | 102070151 | 5/2011 |
| CN | 102198946 | 9/2011 |
| CN | 102208611 | 10/2011 |
| CN | 102208640 | 10/2011 |
| CN | 102290245 | 12/2011 |
| CN | 102306767 | 1/2012 |
| CN | 103178283 | 6/2013 |
| CN | 103227321 | 7/2013 |
| CN | 104584160 | 4/2015 |
| DE | 10157272 | 6/2003 |
| EP | 0 618 629 | 10/1994 |
| EP | 0 875 950 | 11/1998 |
| EP | 1 630 891 | 12/2010 |
| JP | 59139574 | 8/1984 |
| JP | 06-260208 | 9/1994 |
| JP | 06251759 | 9/1994 |
| JP | 07-304984 | 11/1995 |
| JP | 2000-003713 | 1/2000 |
| JP | 3121137 | 12/2000 |
| JP | 2001-176554 | 6/2001 |
| JP | 2003-077445 | 3/2003 |
| JP | 2006-108047 | 4/2006 |
| JP | 2010-155761 | 7/2010 |
| JP | 2012-033366 | 2/2012 |
| KR | 10-2012-0061932 | 6/2012 |
| KR | 10-2012-0125385 | 11/2012 |
| TW | 200740011 | 10/2007 |
| TW | 201016715 | 5/2010 |
| TW | I608647 | 12/2017 |
| WO | WO 2000/055930 | 9/2000 |
| WO | WO 2007/116649 | 10/2007 |
| WO | WO 2012/037171 | 3/2012 |
| WO | WO 2014/014758 | 1/2014 |
| WO | WO 2014/015074 | 1/2014 |
| WO | WO 2014/106088 | 3/2014 |
| WO | WO 2014/059127 | 4/2014 |
| WO | WO 2015/009867 | 1/2015 |
| WO | WO 2016/209655 | 12/2016 |
| WO | WO 2019/182874 | 9/2019 |

OTHER PUBLICATIONS

Bao, Z. et al., "Synthesis of porous self-supporting metal-nanoparticle assemblies with 3D Morphologies inherited from biosilica templates (diatom frustules)" Advanced materials, 2009, v. 21, p. 474.

Baruah, S. et al., "Hydrothermal growth of ZnO nanostructures" Sci. Technol. Adv. Mater., 2009, 10, 013001.

Cai, Y. et al., "Manganese-doped zinc orthosilicate-bearing phosphor microparticles with controlled three-dimentional shapes derived from diatom frustules" Journal of the American Ceramic Society, 2007, 90(4), 1304.

Choma, J. et al., "Deposition of silver nanoparticles on silica spheres and rods" Colloids and Surfaces A: Physicochem. Eng. Aspects, 2012, doi: 10.1016/j.colsurfa.2012.07.004.

Drum, R.W. et al, "Star Trek replicators and diatom nanotechnology" Trends in Biotechnology, 2003, 21(8), 325.

Fang, Y. et al., "Protein-mediated layer-by-layer synthesis of free-standing microscale titania structures with biologically assembled 3-D morphologies" Chemistry of materials, 2009, 21(24), 5704.

Fang, Y. et al., "Synthesis of nanostrcutured Cu- and Ni-based micro-assebies with selectable 3-D hierarchical biogenic morphologies" Journal of Materials Chemistry, 2012, 22(4), 1305.

Flores, J.C. et al., "Variations in morphologies of silver nanoshells on silica spheres" Colloids and Surfaces A: Physicochem. Eng. Aspects, 2008, 330, 86.

Flores, J.C. et al., "Preparation of core-shell nanospheres of silica-silver: $SiO_2@Ag$" Journal of Non-Crystalline Solids, 2008, 354, 5435.

Forsyth et al., "Ionic Liquids—An Overview," Aust. J. Chem., vol. 57, No. 2, Jan. 1, 2004, pp. 113-119.

Franks, G.V. et al., "Zeta potentials and yield stresses of silica suspensions in concentrated monovalent electrolytes: isoelectric point shift and additional attraction" Journal of Colloid and Interfacial Science, 2002, 249, 44.

Gonzalez E. et al., "Surface Analysis of Polymers Treated by Remote Atmospheric Pressure Plasma," Langmuir, 2010, vol. 26(5), pp. 3710-3719.

Gordon, R. et al., "The Glass Menagerie: diatoms for novel application in nanotechnology" Trends Biotechnol., 2009, v.27, p. 116.

Greene, L.E. et al., "General route to vertical ZnO nanowire arrays using textured ZnO seeds" Nano Lett., 2005, 5, 1231.

Gutu, T. et al., "Electron microscopy and optical characterization of cadmium sulphide nanocrystals deposited on the patterned surface of diatom biosilica" Journal of Nanomaterials, vol. 2009, Article ID 860536, 7 pages, Feb. 19, 2009.

Ho et al. "Direct write dispenser printing of a zinc microbattery with an ionic liquid gel electrolyte" Journal of Micromechanics and Microengineering 20 (2010) 104009 (9pp).

Huang et al. "Graphene-based conducting inks for direct inkjet printing of flexible conductive patterns and their applications in electric circuits and chemical sensors" Nano Research (2011), 4(7), 675-684.

International Search Report and Written Opinion in PCT Application No. PCT/US2013/064309, dated Jan. 24, 2014, in 13 pages.

Jeffryes, C. et al., "Peptide mediated deposition of nanostructured $TiO_2$ into the periodic structure of diatom biosilica. Journal of material research" 2008, 23(12), 3255.

Jeffryes, C. et al., "The potential of diatom nanobiotechnology for applications in solar cells, batteries, and electroluminescent devices" Energy & Enviromental Science, 2011, v. 4, p. 3930.

Kalmychkov, G. V. et al., "Method of separation of diatom frustules from bottom sediments for oxygen isotopic analysis and paleoclimatic reconstruction" Geokhimiya, 2005, 12, 1358.

Kim, J. et al., "Direct synthesis and integration of functional nanostructures in microfluidic devices" Lab on Chip, 11, p. 1946-1951, 2011.

Kumar, M. et al., "Chemical vapor deposition of carbon nanotubes: a review on growth mechanism and mass production" Journal of Nanoscience and Nanotechnology, 2010, 10, 3739.

Lebeau T. et al., "Diatom cultivation and biotechnologically relevant products. Part I: cultivation at various scales" Appl. Microbiol. Biotechnol., 2003, 60, 612.

Lee, Seung-Jin et al., "Rapid Hydrolysis of Organophosphorous Esters Induced by Nanostructured, Flourine-Doped Titania Replicas of Diatom Frustules" J. Am. Ceram. Soc., 90 [5], p. 1632-1636, 2007.

Li, H. et al., "Peptide-mediated deposition of nanostructured $TiO_2$ into the periodic structure of diatom biosilica and its integration into

(56) References Cited

OTHER PUBLICATIONS the fabrication of a dye-sensitized solar cell device" Materials Research Society Symposium Proceedings, 2009, 1189E.

Mirkin, C.A. et al., AFOSR Final report. "Diatomeceous, fungal, and bacterial building blocks for material synthesis" 2008.

Nassif, N. et al., "From Fiatoms to silica-based biohybrids" Chem Soc Rev, 2011, v.40, p. 849-859.

Parkinson, J. et al., "Beyond micromashinning: the potential of diatoms" Nanotechnology. 1999, v. 17, p. 190.

Payne, E. K. et al., "Sacrificial Biolofical Templates for the Formation of Nanostructured Metallic Microshells" Chem.,Int. Ed., 2005, v. 44, p. 5064.

Pinkert A. et al., "Ionic Liquids and Their Interaction with Cellulose," Chemical Reviews, 2009, vol. 109, pp. 6712-6728.

Pol, V.G. et al., "Sonochemical Deposition of Silver Nanoparticles on Silica Spheres" Langmuir, 2002, 18, 3352.

Prout, "Aspects of lead/acid battery technology. 7. Separators" Journal of Power Sources (1993), 46(1), 117-38.

Renberg, I. et al., "A procedure for preparing large sets of diatom slides from sediment cores" Journal of Paleolimnology, 1990, 4, 87.

Rings, A. et al., "A new method for the quantitative separation of diatom frustules from lake sediments" Limnology and Oceanography: Methods, 2004, 2, 25.

Round, F. E. et al., "The Diatoms: biology & morphology of the genera" 1990.

Sandhage, K. H. et al., "Novel, Bioclastic Route to Self-Assembled, 3D, Chemically Tailored Meso/Nanostructures: Shape-Preserving Reactive Conversion of Biosilica (Diatom) Microshells" Adv. Mater., 2002, v. 14, No. 6, p. 429-433.

Sandhage, K.H. et al., "Merging biological self-assembly with synthetic chemical tailoring: The potential for 3-D genetically engineered micro/nano-devices (3-D GEMS)" International Journal of Applied Ceramic Technology (2005), 2(4), 317.

Sandhage, K. et al., "Bio-enabled synthesis of functional 3-D nanostructured materials via layer-by-layer deposition" International Chemical Congress of Pacific Basin Societies, Honolulu. 2010.

Serieyssol, K. et al., "Diatom fossils in mires: a protocol for extraction, preparation and analysis in palaeoenvironmental studies" Mires and Peat, 2010, 7, 1.

Shen, Lanyao et al., "Magnesiothermically reduced diatomaceous earth as a porous silicon anode material for lithium ion batteries" Journal of Power Sources (2012), 213, 229-232.

Shian, S. et al., "Three-Dimensional Assemblies of Zirconia Nanocrystals via Shape-Preserving Reactive Conversion of Diatom Microshells" J. Am. Ceram. Soc., 2006, v. 89, p. 694-698.

Skipp, G.L. et al., "Improved density gradient techniques using sodium poltungstate and a comparison to the use of other heavy liquids" U.S. department of the Interior. U.S. Geological survey, 1993, OF 92-038.

Sterrenburg, F.A.S., "How to prepare diatom samples" micrap.selfip. com:81/micrapp/cleandiatoms.pdf, 13 pages, undated.

Sutto et al., "Ionic liquid batteries: Chemistry to replace alkaline/acid energy storage devices", Electrochimica Acta, 2011, vol. 56, pp. 3375-3379.

Tang, S. et al., "Ultrasonic electrodeposition of silver nanoparticles on dielectric silica spheres" Nanotechnology, 2007, 18, 295607.

Torrisi, F. et al. "Ink-jet printed graphene electronics" Condensed Matter (2011), 1-12, arXiv:1111.4970v1.

Toster, J. et al., "Controlling anatase coating of diatom frustules by varying the binding layer" Cryst. Eng. Comm. 2012, 14(2), 3446.

Tuval, T. et al., "A microwave-assisted polyol method for the deposition of silver nanoparticles on silica spheres" Nanotechnology, 2007, 18, 255601.

Umemura, K. et al., "Preparation of photocatalyst using diatom frustules by liquid phase deposition method" Journal of Nanoscience and Nanotechnology, 2010, 10(8), 4883.

Unalan, H.E. et al., "Rapid synthesis of aligned zinc oxide nanowires" Nanotechnology, 2008, 19, 255608.

Wang, Z. et al., "Facile fabrication method and characterization of hollow Ag/SiO2 double-shelled spheres" Langmuir, 2009, 25(13), 7646.

Weatherspoon, M.R. et al., "Thin, conformal, and continues SnO2 coatings on three-dimensional biosilica templates through hydroxyl-group amplification and layer-by-layer alkoxide deposition" Angewandte Chemie, 2007, 46(30), 5724.

Xia, H. et al., "Surface synthesis of zinc oxide nanoparticles on silica spheres: preparation and characterization" J. Phys. Chem. B, 2003, 107, 9175.

Xu, S. et al., "One-dimentional ZnO nanostructures: solution growth and functional properties" NanoRes, 2011, doi 10.1007/s12274-011-0160-7.

Ye, X. et al., "Deposition of silver nanoparticles on silica spheres via ultrasound irradiation" Applied Surface Science, 2007, 253, 6264.

Yu, Y. et al., "Surface modification of diatomaceous earth silica microparticles with functional silanes for metal ions sorption" CHEMECA. Sep. 26-29, 2010, Adelaide, Australia.

Zhang et al. "One-pot synthesis of hierarchical MnO2-modified diatomites for electromechanical capacitor electrodes" Journal of Power Sources, vol. 246, Aug. 6, 2013, pp. 449-456.

Zhang, Y. et al., "Synthesis, characterization, and applications of ZnO nanowires" Journal of Nanomaterials, 2012, doi: 10.1155/2012/624520.

Zheng, S. et al., "Preparation and Photocatalytic Property of TiO2/Diatomite-Based Porous Ceramics Composite Materials" International Journal of Photoenergy, vol. 2012, Article ID 264186, p. 1-4, 2011.

Zhuravlev, "The surface chemistry of amorphous silica. Zhuravlev model" Colloids and Surfaces A: Physicochemical and Engineering Aspects, 2000, 173, 1.

Augustyn et al., "Pseudocapacitive oxide materials for high-rate electrochemical energy storage", Energy Environ. Sci., 2014, vol. 7, pp. 1597-1614.

Guo et al., "Engineering of three dimensional (3-D) diatom@TiO2@MnO2 composites with enhanced supercapacitor performance", Electrochimica acta, 2016, vol. 190, pp. 159-167.

He et al., "Morphology engineering of ZnO nanostructures for high performancce supercapacitors: enhanced electrochemistry of ZnO nanocones compared to ZnO nanowires", Nanotechnology, 2017, vol. 28, in 11 pages.

Huang et al., "MnO2-based nanostructures for high-performance supercapacitors", J. Mater. Chem. A, 2015, vol. 3, pp. 21380-21423.

Le et al., Morphology-controlled MnO2 modified silicon diatoms for high performance asymmetric supercapacitors., J. Mater. Chem. A, 2017, vol. 5, No. 22, pp. 10856-10865.

Li, F et al., "MnO2 nanostructures with three-dimensional (3D) morphology replicated from diatoms for high-performance supercapacitors", J. Mater., Cham. A, 2015, vol. 3, pp. 7855-7861.

Sun et al., "Diatom silica, an emerging biomaterial for energy conversion and storage", J. Mater. Chem. A, 2017, vol. 5, pp. 8847-8859.

Wen et al., Morphology-controlled MnO2-graphene oxide-diatomaceous earth 3-dimentional (3D) composites for high-performance supercapacitors, Dalton Trans., 2016, vol. 45, pp. 936-942.

Wikipedia, "Supercapacitor", https://en.wikipedia.org/wiki/Supercapacitor, downloaded Feb. 8, 2018 in 35 pages.

Zhang et al., "Hierarchical NiO moss decorated diatomites via facile and templated method for high performance supercapacitors", Materials Letters, 2014, vol. 120, pp. 263-266.

International Search Report and Written Opinion received in PCT Application No. PCT/US2014/046910 dated Nov. 18, 2014 in 18 pages.

International Search Report and Written Opinion received in PCT Application No. PCT/US2019/022344 dated Jul. 2, 2019 in 10 pages.

Jian et al., "An Effective Cleaning Method for Producing Pure Diatom Samples from Lake Sediments", Earth and Environment, 2007, vol. 35, No. 1, pp. 91-96.

Huai-Zhi, Cai et al., "Experimental Study on Purification of Sichuan Miyi Diatomite", Comprehensive Utilization of Minerals, 1992, pp. 1-8.

(56) References Cited

OTHER PUBLICATIONS

Peng, Yuan, "Purification of Diatomaceous Earth and its Surface Hydroxyl and Acid Sites", Guangzhou Institute of Geochemistry, Chinese Academy of Sciences, 2001, pp. 9.

Shuilin, Zheng, "Studies of Purifying of Clayey Diatomite", Journal of Wuhan University of Technology—Materials Science, 1994, No. 01, 1 page.

Shuilin, Zheng, "Studies of Purifying of Clayey Diatomite", Journal of Wuhan University of Technology—Materials Science, 1994, No. 01, pp. 125-133.

\* cited by examiner

PRINTED ENERGY STORAGE DEVICE

CROSS REFERENCE TO RELATED APPLICATIONS

This application is a continuation of U.S. patent application Ser. No. 15/374,699, filed Dec. 9, 2016, entitled "PRINTED ENERGY STORAGE DEVICE," which is a continuation of U.S. patent application Ser. No. 14/050,145, filed Oct. 9, 2013, entitled "PRINTED ENERGY STORAGE DEVICE," now U.S. Pat. No. 9,520,598, which claims the benefit of U.S. Provisional Patent Application Ser. No. 61/712,219, filed Oct. 10, 2012, entitled "PRINTED ENERGY STORAGE DEVICE," both of which are incorporated herein by reference in their entireties.

BACKGROUND

Field

This invention relates to energy storage devices, particularly to printed energy storage devices.

Description of the Related Art

Thin and flexible energy storage devices are needed for powering thin and/or small electronic devices in the consumer market. For example, lights and sound in greeting cards, thin advertisement tools like magazine inserts, skin care products, safe pass cards, some miniature medical devices, etc. can be powered by using thin batteries. Some thin batteries already exist on the market (e.g., zinc carbon batteries produced by Enfucell Oy Ltd. of Vantaa, Finland and Blue Spark Technologies, Inc. of Westlake, Ohio, and lithium polymer batteries produced by Solicore, Inc. of Lakeland, Fla.). These batteries generally have a thickness from about 0.45-0.7 mm. They are sealed in a pouch unit cells with two poles for wired connection to devices which need power.

Zinc-manganese dioxide ($Zn/MnO_2$) batteries are primary batteries (e.g., one time use). These batteries can be filled with an aqueous solution of zinc and ammonia salts or potassium hydroxide. They have an initial voltage of 1.5-1.6V and are designed for low or moderate current drain. Shelf life of these batteries is 1-3 years. Main advantages of $Zn/MnO_2$ batteries are cost and safety. They are the most affordable batteries on the market due to cheap and abundant raw materials for the battery build. These materials are considered "green" due to non-toxicity.

SUMMARY

A printed energy storage device, for example a printed zinc manganese-dioxide ($Zn/MnO_2$) battery, may have a layer that includes an ionic liquid, where the ionic liquid has a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium. The ionic liquid may include an anion selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl) phosphinate, iodide, chloride, bromide, and nitrate. The printed energy storage device may have a first electrode, a second electrode and a separator positioned between the first electrode and the second electrode, where at least one of the first electrode, the second electrode and the separator includes the ionic liquid. In some embodiments, the ionic liquid includes 1-ethyl-3-methylimidazolium tetrafluoroborate ($C_2mimBF_4$).

In some embodiments, the first electrode can include the ionic liquid. In some embodiments, the second electrode can include the ionic liquid. In some embodiments, the separator can include the ionic liquid.

The printed energy storage device may include an intermediate layer. The intermediate layer may be between the first electrode and the separator. The intermediate layer may be between the second electrode and the separator. In some embodiments, the intermediate layer includes the ionic liquid.

The printed energy storage device may include a current collector coupled to the first electrode or the second electrode.

In some embodiments, at least one of the first electrode, the second electrode, the separator, the intermediate layer, and the current collector includes a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycol-hexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organo-modified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, at least one of the first electrode, the intermediate layer, and the separator includes a salt. The salt may include a zinc salt. In some embodiments, the anion of the ionic liquid is the same as an anion of the salt. The salt may include zinc tetrafluoroborate and the ionic liquid may include 1-ethyl-3-methylimidazolium tetrafluoroborate. In some embodiments, the salt can include zinc chloride. In some embodiments, the salt can include zinc bis(trifluoromethanesulfonyl)imide. In some embodiments, the salt can include zinc sulfate. In some embodiments, the salt can include zinc nitrate. In some embodiments, the salt can include zinc carbonate.

In some embodiments, at least one of the first electrode and the second electrode includes polyvinylidene difluoride.

In some embodiments, at least one of the second electrode and the current collector can include carbon nanotubes. The carbon nanotubes may include single-wall carbon nanotubes. The carbon nanotubes may include multi-wall carbon nanotubes.

The second electrode may have a homogeneous paste comprising the carbon nanotubes and the ionic liquid. The second electrode may have manganese dioxide. In some embodiments, the second electrode can include a conductive carbon. The conductive carbon can include graphite.

In some embodiments, the current collector can have at least one of nickel flakes, graphene flakes, and graphite powder. The current collector may have nickel flakes. The current collector may have graphene flakes. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder. In some embodiments, the current collector can have polyvinylidene difluoride.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns. In some embodiments, the separator can include polyvinylidene difluoride.

A layer of a printed energy storage device, for example a printed zinc manganese-dioxide ($Zn/MnO_2$) battery, may include a salt having an anion, and an ionic liquid including the anion.

In some embodiments, the ionic liquid can include a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium.

In some embodiments, the anion can be selected from the group consisting of tetrafluoroborate, tris(pentafluoroethyl) trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl) phosphinate, iodide, chloride, bromide, and nitrate.

In some embodiments, the ionic liquid can include 1-ethyl-3-methylimidazolium tetrafluoroborate (C2mimBF4). In some embodiments, the salt can include a zinc salt. The salt may include zinc tetrafluoroborate. In some embodiments, the salt can include zinc chloride. In some embodiments, the salt can include zinc bis(trifluoromethanesulfonyl)imide. In some embodiments, the salt can include zinc sulfate. In some embodiments, the salt can include zinc nitrate. In some embodiments, the salt can include zinc carbonate.

The printed energy storage device may have a first electrode, a second electrode, and a separator between the first electrode and the second electrode. In some embodiments, the printed energy storage device can include an intermediate layer. The intermediate layer may be between the first electrode and the separator. The intermediate layer may be between the second electrode and the separator. In some embodiments, the printed energy storage device can include a current collector electrically coupled to the first electrode or the second electrode.

The layer may be the first electrode, the separator, and/or the intermediate layer.

In some embodiments, at least one of the first electrode, the second electrode, the separator, the intermediate layer, and the current collector can have a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycol-hexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, at least one of the first electrode, the second electrode, the separator, and the current collector can have polyvinylidene difluoride.

In some embodiments, at least one of the second electrode and the current collector can have carbon nanotubes. The carbon nanotubes may include single-wall carbon nanotubes. The carbon nanotubes may include multi-wall carbon nanotubes.

The second electrode may have a mixture including the carbon nanotubes and the ionic liquid. The second electrode may have manganese dioxide. In some embodiments, the second electrode can include a conductive carbon. The conductive carbon can include graphite.

In some embodiments, the current collector can have at least one of nickel flakes, graphene flakes, and graphite powder. The current collector may have nickel flakes. The current collector may have graphene flakes. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns.

In some embodiments, the intermediate layer can include polyvinyl alcohol.

A layer of a printed energy storage device, for example a printed zinc manganese-dioxide ($Zn/MnO_2$) battery, may have a salt including zinc tetrafluoroborate, and an ionic liquid having 1-ethyl-3-methylimidazolium tetrafluoroborate.

The printed energy storage device may include a first electrode, a second electrode, and a separator between the first electrode and the second electrode. In some embodiments, the printed energy storage device can include an intermediate layer. The intermediate layer may be between the first electrode and the separator. The intermediate layer may be between the second electrode and the separator. In some embodiments, the printed energy storage device can include a current collector electrically coupled to the first electrode or the second electrode.

The layer may be the first electrode, the separator, and/or the intermediate layer.

In some embodiments, at least one of the first electrode, the second electrode, the separator, the intermediate layer, and the current collector can have a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycol-hexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organo-modified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, at least one of the first electrode, the second electrode, the separator, and the current collector can have polyvinylidene difluoride.

In some embodiments, at least one of the second electrode and the current collector can have carbon nanotubes. The carbon nanotubes may include single-wall carbon nanotubes. The carbon nanotubes may include multi-wall carbon nanotubes.

The second electrode may have a mixture including the carbon nanotubes and the ionic liquid. The second electrode may have manganese dioxide. In some embodiments, the second electrode can include a conductive carbon. The conductive carbon can include graphite.

In some embodiments, the current collector can have at least one of nickel flakes, graphene flakes, and graphite powder. The current collector may have nickel flakes. The current collector may have graphene flakes. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns.

In some embodiments, the intermediate layer can include polyvinyl alcohol.

A planarization adhesion layer of a printed energy storage device, for example a printed zinc manganese-dioxide (Zn/$MnO_2$) battery, can include polyvinyl alcohol, a salt, an ionic liquid, where the ionic liquid can include a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl) phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and where the ionic liquid can include an anion selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl) phosphinate, iodide, chloride, bromide, and nitrate.

In some embodiments, the salt can include an anion that is the same as the anion of the ionic liquid. In some embodiments, the salt can include a zinc salt. The salt may include zinc tetrafluoroborate and the ionic liquid can include 1-ethyl-3-methylimidazolium tetrafluoroborate. In some embodiments, the salt can include zinc chloride. In some embodiments, the salt can include zinc bis(trifluoromethanesulfonyl)imide. In some embodiments, the salt can include zinc sulfate. In some embodiments, the salt can include zinc nitrate. In some embodiments, the salt can include zinc carbonate.

The printed energy storage device may have a first electrode, a second electrode, and a separator between the first electrode and the second electrode.

The planarization adhesion layer may be between the first electrode and the separator. The planarization adhesion layer may be between the second electrode and the separator. In some embodiments, the printed energy storage device can include a current collector electrically coupled to the first electrode or the second electrode. In some embodiments, the printed energy storage device can include a current collector electrically coupled to the first electrode or the second electrode.

In some embodiments, at least one of the first electrode, the second electrode, the separator, the planarization adhesion layer, and the current collector can have a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, at least one of the first electrode, the second electrode, the separator, and the current collector can have polyvinylidene difluoride.

In some embodiments, at least one of the second electrode and the current collector can have carbon nanotubes. The carbon nanotubes may include single-wall carbon nanotubes. The carbon nanotubes may include multi-wall carbon nanotubes.

The second electrode may have a mixture including the carbon nanotubes and the ionic liquid. The second electrode may have manganese dioxide. In some embodiments, the second electrode can include a conductive carbon. The conductive carbon can include graphite.

In some embodiments, the current collector can have at least one of nickel flakes, graphene flakes, and graphite powder. The current collector may have nickel flakes, for example a current collector electrically coupled to the first electrode. The current collector may have graphene flakes, for example a current collector electrically coupled to the second electrode. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns.

In some embodiments, at least one of the first electrode, separator, and second electrode can include the ionic liquid.

An electrode of a printed energy storage device, for example a printed zinc manganese-dioxide ($Zn/MnO_2$) battery, can include carbon nanotubes, and an ionic liquid, where the ionic liquid can include a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl) phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and where the ionic liquid can include an anion selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl) phosphinate, iodide, chloride, bromide, and nitrate.

The carbon nanotubes may include single-wall carbon nanotubes. The carbon nanotubes may include multi-wall carbon nanotubes. The carbon nanotubes may be ground. In some embodiments, the carbon nanotubes and the ionic liquid can form a homogeneous mixture.

In some embodiments, the ionic liquid can include 1-ethyl-3-methylimidazolium tetrafluoroborate.

In some embodiments, the electrode can include manganese dioxide. In some embodiments, the electrode can include graphite powder.

The printed energy storage device may further include a second electrode and a separator between the electrode and the second electrode.

In some embodiments, the printed energy storage device can include an intermediate layer. The intermediate layer may be between the first electrode and the separator. The intermediate layer may be between the second electrode and the separator. In some embodiments, the printed energy storage device can include a current collector electrically coupled to the first electrode or the second electrode.

In some embodiments, at least one of the second electrode, the separator, and the intermediate layer can include the ionic liquid. In some embodiments, at least one of the second electrode, the separator, and the intermediate layer can include a salt. The salt may include an anion that is the same as an anion of the ionic liquid.

In some embodiments, the salt can include a zinc salt. In some embodiments, the ionic liquid can include 1-ethyl-3-methylimidazolium tetrafluoroborate (C2mimBF4) and the salt can include zinc tetrafluorborate. In some embodiments, the salt can include zinc chloride. In some embodiments, the salt can include zinc bis(trifluoromethanesulfonyl)imide. In some embodiments, the salt can include zinc sulfate. In some embodiments, the salt can include zinc nitrate. In some embodiments, the salt can include zinc carbonate.

In some embodiments, at least one of the first electrode, the second electrode, the separator, the intermediate layer, and the current collector can have a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organo-modified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, at least one of the electrode, the second electrode, the separator, and the current collector can include polyvinylidene difluoride.

In some embodiments, the current collector can have at least one of nickel flakes, graphene flakes, and graphite powder. The current collector may have nickel flakes, for example a current collector coupled to the second electrode. The current collector may have graphene flakes, for example a current collector coupled to the first electrode. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns.

In some embodiments, the intermediate layer can include polyvinyl alcohol.

A printed energy storage device, for example a printed zinc manganese-dioxide (Zn/MnO$_2$) battery, can include a first electrode having zinc, a second electrode having manganese dioxide, a separator between the first electrode and the second electrode, and a current collector electrically connected to the first electrode or the second electrode, the current collector including conductive flakes.

In some embodiments, the current collector can include carbon nanotubes. The carbon nanotubes may include single-wall carbon nanotubes. The carbon nanotubes may include multi-wall carbon nanotubes.

In some embodiments, the conductive flakes can include at least one of nickel flakes, graphene flakes, and graphite powder. The current collector may have nickel flakes, for example a current collector electrically coupled to the first electrode. The current collector may have graphene flakes, for example a current collector electrically coupled to the second electrode. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder.

In some embodiments, the printed energy storage device can include an intermediate layer. The intermediate layer may be between the first electrode and the separator. The intermediate layer is between the second electrode and the separator.

In some embodiments, at least one of the first electrode, the second electrode, the separator and the intermediate layer can include an ionic liquid, where the ionic liquid can include a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, where the ionic liquid can include an anion selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

In some embodiments, the ionic liquid can include 1-ethyl-3-methylimidazolium tetrafluoroborate (C2mimBF4).

In some embodiments, at least one of the first electrode, the separator, and the intermediate layer can include a salt. The salt may include an anion that is the same as the anion of the ionic liquid. In some embodiments, the salt can include zinc tetrafluoroborate and the ionic liquid can include 1-ethyl-3-methylimidazolium tetrafluoroborate.

In some embodiments, the salt can include zinc chloride. In some embodiments, the salt can include zinc bis(trifluoromethanesulfonyl)imide. In some embodiments, the salt can include zinc sulfate. In some embodiments, the salt can include zinc nitrate. In some embodiments, the salt can include zinc carbonate.

In some embodiments, the first electrode can include polyvinylidene difluoride.

In some embodiments, at least one of the first electrode, the second electrode, the separator, the intermediate layer, and the current collector can include a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organo-modified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, the second electrode can include the carbon nanotubes. In some embodiments, the second electrode can include a homogeneous paste including the carbon nanotubes and the ionic liquid. In some embodiments, the second electrode can include a conductive carbon. The conductive carbon can include graphite powder.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns.

In some embodiments, the intermediate layer can include polyvinyl alcohol.

A conductive paste for a layer of a printed energy storage device, for example a printed zinc manganese-dioxide (Zn/MnO$_2$) battery, can include carbon nanotubes, and an ionic liquid, where the ionic liquid can include a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and where the ionic liquid can include an anion selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl) phosphinate, iodide, chloride, bromide, and nitrate.

In some embodiments, the ionic liquid can include 1-ethyl-3-methylimidazolium tetrafluoroborate (C2mimBF4).

The carbon nanotubes may include single-wall carbon nanotubes. The carbon nanotubes may include multi-wall carbon nanotubes. The carbon nanotubes may be ground. In some embodiments, the carbon nanotubes and the ionic liquid can form a homogeneous mixture.

In some embodiments, the layer can be a first electrode. The first electrode can include manganese dioxide. In some embodiments, the first electrode can include graphite.

In some embodiments, a printed energy storage device can include a second electrode and a separator between the first electrode and the second electrode.

In some embodiments, the printed energy storage device can include an intermediate layer. The intermediate layer may be between the first electrode and the separator. The intermediate layer may be between the second electrode and the separator. In some embodiments, the printed energy storage device can include a current collector electrically coupled to the first electrode or the second electrode.

In some embodiments, at least one of the second electrode, the separator, and the intermediate layer can include the ionic liquid. In some embodiments, at least one of the second electrode, the separator, and the intermediate layer can include a salt. In some embodiments, the salt can include a zinc salt. In some embodiments, the salt can include an anion that is the same as the anion of the ionic liquid. The salt may include zinc tetrafluoroborate and the ionic liquid can include 1-ethyl-3-methylimidazolium tetrafluoroborate. In some embodiments, the salt can include zinc chloride. In some embodiments, the salt can include zinc bis(trifluoromethanesulfonyl)imide. In some embodiments, the salt can include zinc sulfate. In some embodiments, the salt can include zinc nitrate. In some embodiments, the salt can include zinc carbonate.

In some embodiments, at least one of the first electrode, the second electrode, the separator, the intermediate layer, and the current collector can have a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

In some embodiments, at least one of the first electrode, the second electrode, the separator, and the current collector can include polyvinylidene difluoride.

In some embodiments, the current collector can include the carbon nanotubes.

In some embodiments, the current collector can have at least one of nickel flakes, graphene flakes, and graphite powder. The current collector may have nickel flakes, for example a current collector electrically coupled to the second electrode. The current collector may have graphene flakes, for example a current collector electrically coupled to the first electrode. The current collector may have nickel flakes and graphene flakes. The current collector may have nickel flakes, graphene flakes, and graphite powder. The current collector may have nickel flakes and carbon nanotubes. The current collector may have nickel flakes, graphene flakes, and carbon nanotubes. The current collector may have nickel flakes, graphene flakes, carbon nanotubes, and graphite powder. The current collector may have nickel flakes, carbon nanotubes, and graphite powder.

In some embodiments, the separator can have microspheres. The microspheres may include at least one of glass, alumina, silica, polystyrene, and melamine. The microspheres may be hollow. The microspheres may be solid. In some embodiments, the microspheres can have a diameter from about 0.5 microns to about 30 microns.

In some embodiments, the intermediate layer can include polyvinyl alcohol.

For purposes of summarizing the invention and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the invention may be embodied or carried out in a manner that can achieve or optimize one advantage or a group of advantages without necessarily achieving other objects or advantages.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

These and other features, aspects, and advantages of the present disclosure are described with reference to the drawings of certain embodiments, which are intended to illustrate certain embodiments and not to limit the invention.

DETAILED DESCRIPTION

Figure 1:
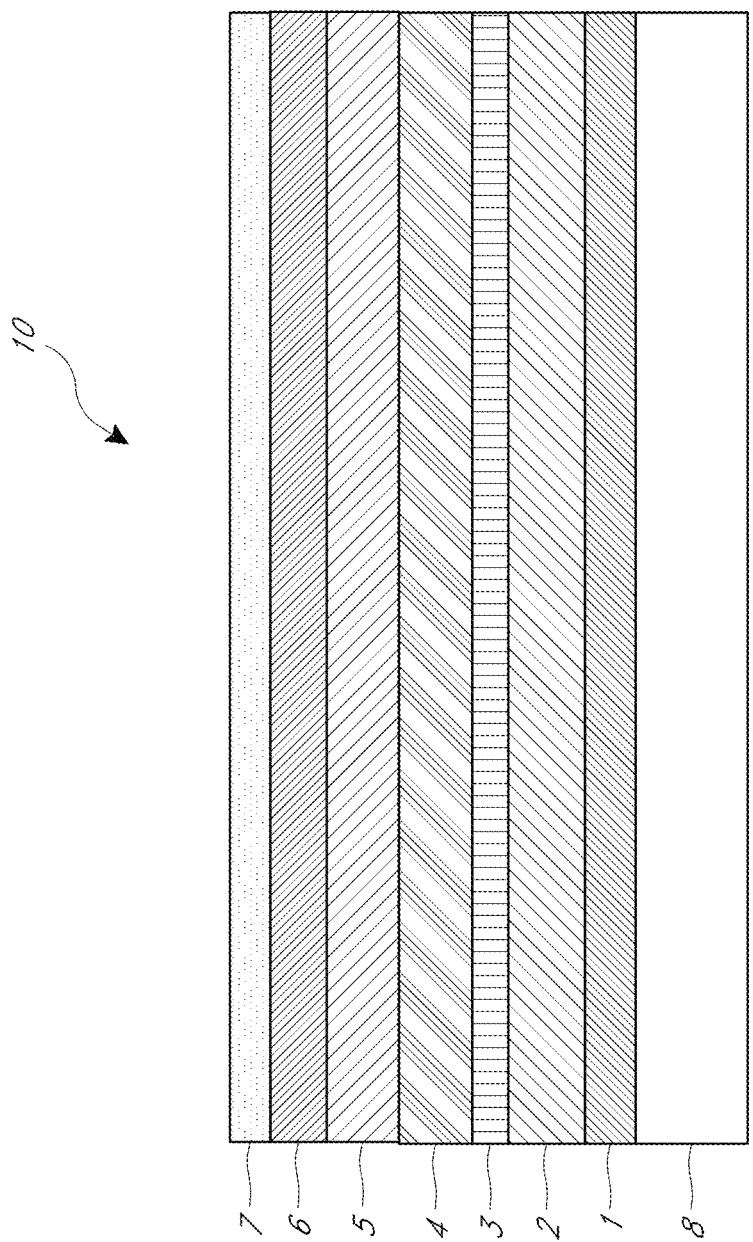
FIG. 1 is a cross-sectional or side elevational view of an example embodiment of a printed battery.

Although certain embodiments and examples are described below, those of skill in the art will appreciate that the invention extends beyond the specifically disclosed embodiments and/or uses and obvious modifications and equivalents thereof. Thus, it is intended that the scope of the invention herein disclosed should not be limited by any particular embodiments described below.

In some embodiments, a zinc-manganese dioxide (Zn/MnO$_2$) battery comprises all elements of which are printed. For example, all components of the battery, including current collectors, electrodes, battery separator, and leads may be sequentially printed onto one substrate. Printing can be a scalable, cost effective, and productive technique.

In some embodiments, printed Zn/MnO$_2$ batteries can have a thickness from about 0.1 mm to about 0.4 mm and can be flexible depending on the substrate that at least some of the battery layers are printed on. Printed zinc-manganese dioxide batteries can be used as a separate device or integrated on a substrate with other electronic components, such as light-emitting diode (LED) lights. Devices into which printed zinc-manganese dioxide batteries may be integrated devices can be thin and/or flexible. An integrated printed zinc-manganese dioxide battery may not need additional connection elements like wires for electrical connection with other electronics as all necessary connections may also be printed.

A fully printed battery can enable fabrication of batteries having a variety of shapes. In some embodiments, a printed battery can be printed around other components of an integrated device and/or printed on a substrate with an unusual shape. For example, the printed battery may be printed on commercially available substrates (e.g., polyimide film such as Kapton® from DuPont, Inc. of Wilmington, Del.) or manufactured. In some embodiments, one printed battery can be printed above one or more other energy storage devices, including, for example, one or more other printed batteries. For example, the printed battery can be connected with one or more other printed batteries in parallel to enable an increased energy storage capacity per unit of area and/or in series to enable an increased working voltage. Suitable zinc (Zn) for a printed battery may be commercially available (e.g., from Teck American Inc., of Spokane, Wash.) or manufactured. Suitable manganese dioxide (MnO$_2$) may be commercially available (e.g., Minera Autlan, of Mexico) or manufactured.

In some embodiments, a printed Zn/MnO$_2$ battery has an open circuit potential from about 1.5 volts (V) to about 1.55V and a capacitance of about 0.1 mAh/cm$^2$ when discharged at about 0.1 mA/cm$^2$. For example, three 1×1.5 inch printed zinc-manganese dioxide batteries connected in series printed on a substrate with 30 blue micro-light-emitting-diodes (microLEDs) can light the microLEDs non-stop for 1.5 hours. In some embodiments, printed batteries can be integrated into a greeting and/or a business card. An on-off switch (e.g., a press-button control) for the LEDs can further extend the operating life of batteries.

In some embodiments, a printed zinc-manganese dioxide includes an electrolyte comprising ionic liquid 1-ethyl-3-methylimidazolium tetrafluoroborate (C$_2$mimBF$_4$). The ionic liquid may be commercially available (e.g., IoLiTec Ionic Liquids Technologies GmbH, of Heilbronn, Germany) or manufactured. In certain embodiments, the electrolyte for Zn/MnO$_2$ batteries may comprise a "green" electrolyte-ionic liquid 1-ethyl-3-methylimidazolium tetrafluoroborate (C$_2$mimBF$_4$). Some existing Zn/MnO$_2$ batteries (comprising zinc carbon and zinc alkaline) have either an aqueous solution of ammonium and zinc chlorides or an aqueous solution of potassium hydroxide as electrolytes. Aqueous electrolytes can evaporate easily, including for example after integration into a battery, and special measures may need to be taken to inhibit or prevent evaporation or leakage. A battery having an aqueous electrolyte may require special care during battery assembly. C$_2$mimBF$_4$ is a non-volatile electrolyte. Non-volatile electrolytes may be suitable for printing processes. For example, an electrolyte may maintain or substantially maintain a concentration during a battery production process and/or in post assembly life of a battery comprising the electrolyte. Ionic liquids are ecological "green" electrolytes in terms that they do not contaminate air. Another attractive property of the ionic liquid used is non-flammability. For example, an ionic liquid electrolyte cannot self-ignite during a battery overload or shortage, and will not support any flame.

FIG. 1 is a cross-sectional or side elevational view of an example embodiment of the a printed battery 10, for example a zinc-manganese dioxide battery. The printed battery 10 includes a first current collector 1, a first electrode layer 2, an intermediate layer 3, a separator layer 4, a second electrode layer 5, a second current collector 6, an insulator layer 7, and a substrate 8. The first current collector 1 is configured provide electrical contact between the first electrode layer 2 and an external circuit. In some embodiments, the printed battery 10 may optionally not include the intermediate layer 3. In some embodiments, the current collector 6 is configured to provide electrical contact between the second electrode layer 5 and an external circuit. In some embodiments, the printed battery 10 may optionally not include the current collector 1, for example in embodiments in which the substrate 8 comprises a material having conductivity allowing connection to an external circuit. In some embodiments, the intermediate layer 3 comprises a plurality of layers. In some embodiments, the printed battery 10 may optionally not include the intermediate layer 3.

In some embodiments, the printed battery 10 can be printed layer by layer. For example, layers 1-7 of the printed zinc manganese dioxide battery 10 may be printed one above the other in the following sequence: the first current collector layer 1 may be printed onto a surface of the substrate 8; the first electrode layer 2 may be printed onto a surface of the first current collector layer 1; the intermediate layer 3 may be printed onto a surface of the first electrode layer 2; the separator layer 4 may be printed onto a surface of the intermediate layer 3, or as described herein onto a surface of the first electrode layer 2; the second electrode layer 5 may be printed onto a surface of the separator layer 4; the second current collector layer 6 may be printed onto a surface of the second electrode layer 5; and the insulator layer 7 may be printed onto a surface of the current collector layer 6. The insulator layer 7 may comprise a polymer and may provide the printed battery 10 with a seal (e.g., a hermetic seal).

Figure 2:
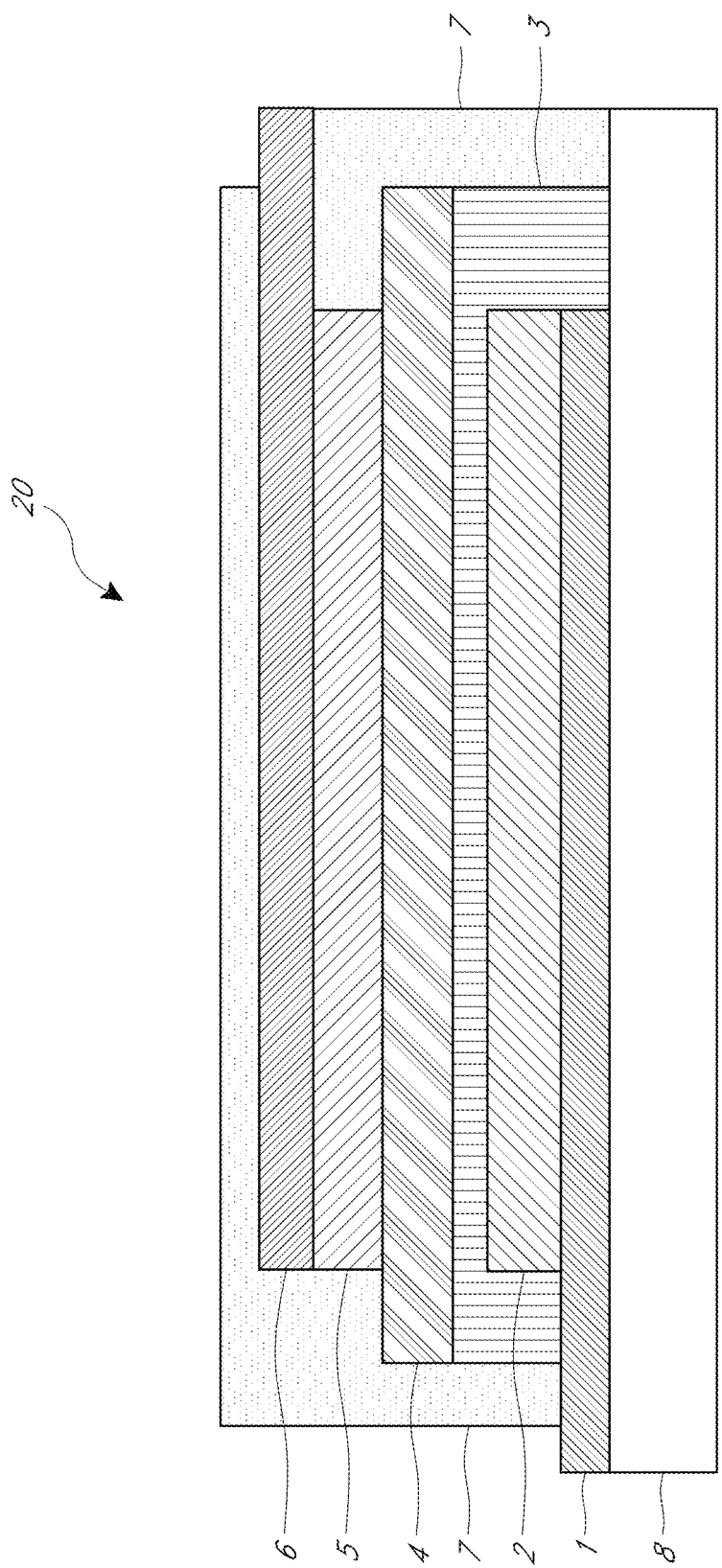
FIG. 2 is a cross-sectional or side elevational view of another example printed battery.

FIG. 2 is a cross-sectional or side elevational view of another example embodiment of a printed battery 20, for example a zinc-manganese dioxide battery comprising the layers 1-8 discussed herein. The current collector layers 1, 6 may extend beyond a portion of electrode layers 2, 5, for example to facilitate coupling with an external circuit. The intermediate layer 3 may form an enclosure over at least a portion of electrode layer 2, for example to facilitate separation between the two electrode layers 2, 5. The polymer insulator layer 7 may form an enclosure around the electrode layers 2, 5, the intermediate layer 3, and the separator layer 4, for example to seal the layers of the printed battery 10 (e.g., with a hermetic seal).

In some embodiments, a zinc anode (e.g., the first electrode layer 2 in FIG. 1) may comprise a polymer binder (e.g., high molecular weight polyvinylidene difluoride polymer), zinc, and/or an electrolyte comprising zinc salt such as zinc tetrafluoroborate ($ZnBF_4$) and $C_2mimBF_4$ ionic liquid. The zinc salt has a common anion with the used ionic liquid and can create an electroactive couple with zinc ($Zn/Zn^{2+}$).

In some embodiments, the separator layer 4 can comprise an electrolyte/polymer gel and microspheres (e.g., micro glass spheres as described in U.S. patent application Ser. No. 13/223,279, entitled "Printable Ionic Gel Separation Layer for Energy Storage Devices," which is herein incorporated by reference in its entirety). For example, a printed zinc manganese-dioxide battery may comprise a separator layer including an electrolyte comprising $ZnBF_4/C_2mimBF_4$, a polymeric gel comprising copolymers of polyvinylidene difluoride, and micro glass spheres. Micro glass spheres may be commercially available (e.g., from Potters Industries, of Brownwood, Tex.) or manufactured. Some commercially available batteries, including flexible batteries, use a separate sheet of membrane as a separator between electrode layers. A separator comprising solid microspheres is that the separator layer 4 may advantageously be printed. For example, the separator layer 4, including solid microspheres may be fabricated through a printing process, along with other components of a printed battery 10, instead of being formed during a separate fabrication process and then being integrated into the battery. Ionic conduction through the separator layer 4 may be realized by the ionic liquid/polymer gel. The polymer gel can be fabricated from polyvinylidene difluoride copolymer. The solid microspheres can enable the separator layer 4 to withstand applied pressure during the printing process, including for example subsequent printing of one or more other layers 5-7 of the printed battery 10 and, therefore, inhibit or prevent shorting of the printed battery 10. A printed battery 10 including a printed separator layer 4 comprising solid microspheres can provide larger or significantly larger charge storage areas than batteries including a non-printed separator, for example because the separator layer 4 can be printed over a large surface area and/or have unique lateral shapes.

A printed battery 10 may optionally comprise the intermediate layer 3. The intermediate layer 3 may be an ultrathin layer (e.g., having a thickness in a range from about 1 micron (rpm) to about 3 microns) that coats an underlying layer, for example the first electrode layer 2. The printed battery 10 may include an intermediate layer between other layers described herein, including, for example, between the separator layer 4 and the second electrode layer 5. The intermediate layer 3 can provide a smoother interface between two adjacent printed layers and/or help preserve the structural integrity of one or more underlying layers from damage due to pressure applied during printing of one or more subsequent layers (e.g., during printing of the separator layer 4). The intermediate layer 3 may also promote adhesion between the two adjacent layers, such as between the separator layer 4 and the first electrode layer 2. In some embodiments, the intermediate layer 3 comprises a polymeric gel and an electrolyte for ionic conduction. The electrolyte may comprise an ionic liquid, such as the same ionic liquid as the separator layer 4. The polymeric gel can be made from polyvinyl alcohol (PVA) polymers having different molecular masses. For example, the intermediate layer 3 may include an electrolyte comprising $ZnBF_4/C_2mimBF_4$ and a polymeric gel comprising polyvinyl alcohol. Other polymers and/or electrolytes may also be suitable.

In some embodiments, an electrode layer (e.g., the first electrode layer 2, the second electrode layer 5) can include carbon nanotubes (CNT). For example, a printed zinc manganese-dioxide battery cathode (e.g., the second electrode layer 5 of the printed battery 10) may comprise $MnO_2$, conductive carbon (e.g., graphite), a polymer (e.g., high molecular weight polyvinylidene difluoride polymer) as a binder, an electrolyte (e.g. an ionic liquid), and carbon nanotubes. Suitable graphite may be commercially available (e.g., from TIMCAL Ltd., of Westlake, Ohio) or manufactured. The printed zinc manganese-dioxide battery cathode may comprise a dispersion comprising ground carbon nanotubes and an ionic liquid (e.g., $C_2mimBF_4$). Carbon nanotubes may include single-wall (SWCNT) and/or multi-wall carbon nanotubes (MWCNT). Carbon nanotubes may be commercially available (e.g., from SouthWest NanoTechnologies Inc., of Norman, Okla.) or manufactured. The second electrode layer 5 may include a homogeneous paste comprising an ionic liquid and carbon nanotubes. Incorporation of carbon nanotubes into an electrode may improve electron conductivity within the electrode and/or facilitate incorporation of ionic liquid electrolyte in the electrode.

The composition of the current collector layers 1 and 6 may differ depending on the functions that each is designed to fulfill. The first current collector layer 1, for example configured to be at the bottom of a printed stack and/or to be electrically coupled to an anode, may comprise a mixture of nickel (Ni) flakes and a polymer, and may be printed on the substrate 8 to provide good adherence of the first electrode layer 1 to the substrate 8. Nickel flakes may be commercially available (e.g., from Novamet Specialty Products Corp. of Wyckoff, N.J.) or manufactured. The second current collector layer 6, for example configured to electrically couple to a cathode, may comprise graphene flakes and a polymer, and may be printed over the second electrode layer 5. Graphene flakes may be commercially available (e.g., from XG Sciences, Inc. of Lansing, Mich.) or manufactured. Graphene particles in the second current collector layer 6 are generally light and bendable such that they do not penetrate through the second electrode layer 5 during printing of the second current collector layer 6.

Example combinations of conductive materials for current collectors comprise:
1) Ni flakes
2) Graphene flakes
3) Ni and graphene flakes
4) Ni flakes, graphene and graphite powder
5) Ni flakes, CNTs
6) Ni flakes, graphene, CNTs
7) Ni flakes, graphene, CNTs, graphite powder
8) Ni flakes, CNTs, graphite powder
9) Graphene, CNTs
10) Graphene, CNTs, graphite powder.

A polymer insulator layer 7, such as a hermetic printed layer, may optionally be used to seal the printed battery 10, for example to inhibit or prevent contact between the atmosphere (e.g., water and oxygen) with the materials of the printed battery 10. The insulator layer 7 may comprise, for example, an environmentally robust polymer.

Printing

The final composition of the layers may be formed after printing a corresponding ink and drying (curing) the layer at least a certain temperature for at least a certain time.

Inks generally have all the components of the corresponding layers plus one or more organic solvents. The solvents can be used to dissolve polymers (e.g., acting as solvents) and/or to create a suitable viscosity for printing of the inks (e.g., acting as viscosity modifiers) that evaporate during the drying process.

The printed zinc manganese dioxide battery can be printed on any flexible or rigid substrate that is conductive or non-conductive. Choice of organic solvents often depends on the ability of the solvent to wet substrates (e.g., acting as wetting agents). In some embodiments, a printing ink comprises a second solvent to provide increased wettability of the substrate.

In some embodiments, the printing ink is suitable for a screen printing process. The printing ink may also be suitable for other printing processes.

Battery Performance Measurement

Figure 3B:
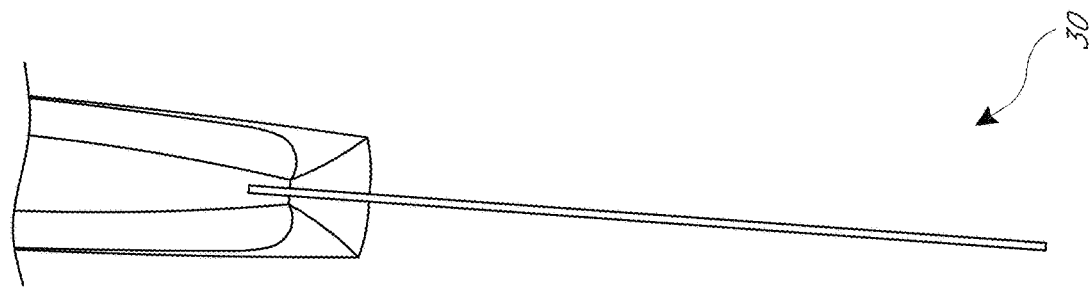
FIG. 3B is a photographic side view of the printed battery of FIG. 3A.
Figure 3A:
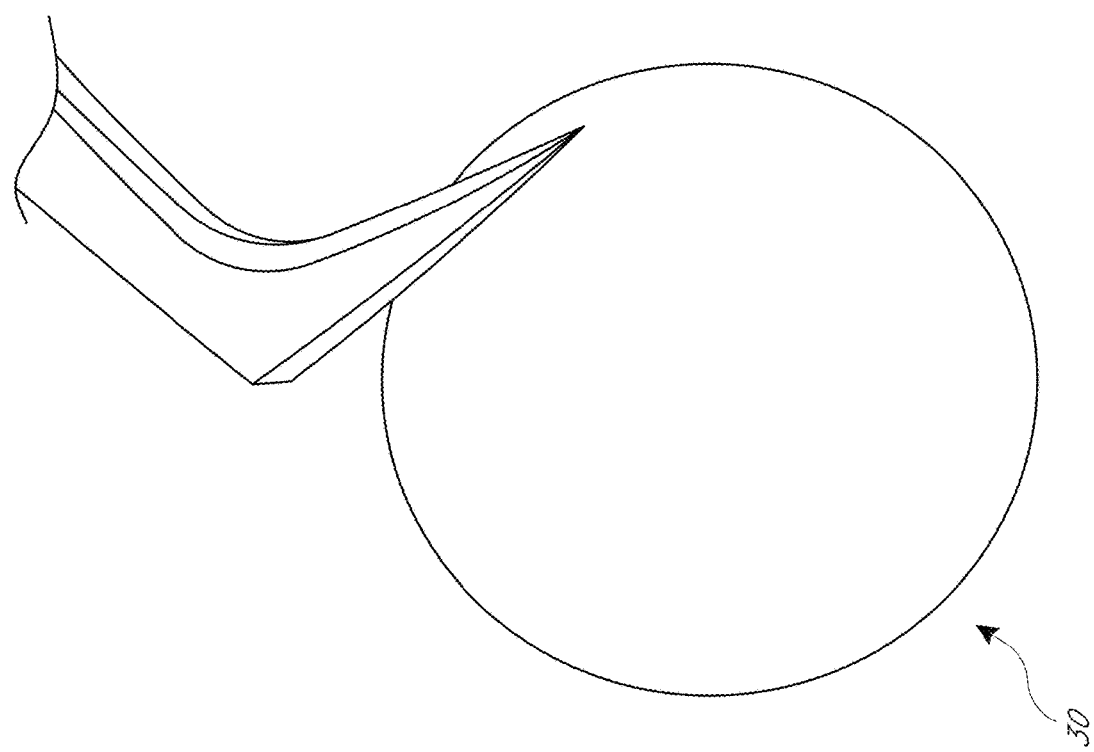
FIG. 3A is a photographic plan view of an example embodiment of a printed battery.

Printed zinc manganese dioxide ($Zn/MnO_2$) batteries may be printed in different designs depending on testing procedure. The batteries discharged in electrochemical cells can be printed on aluminum (Al) foil without current collectors. FIGS. 3A and 3B illustrate an example printed $Zn/MnO_2$ battery on Al foil. FIG. 3A is a photographic plan view of an example embodiment of a printed battery, and FIG. 3B is a photographic side view of the printed battery of FIG. 3A. The electrochemical cell can then connect to a potentiostat.

Figure 4:
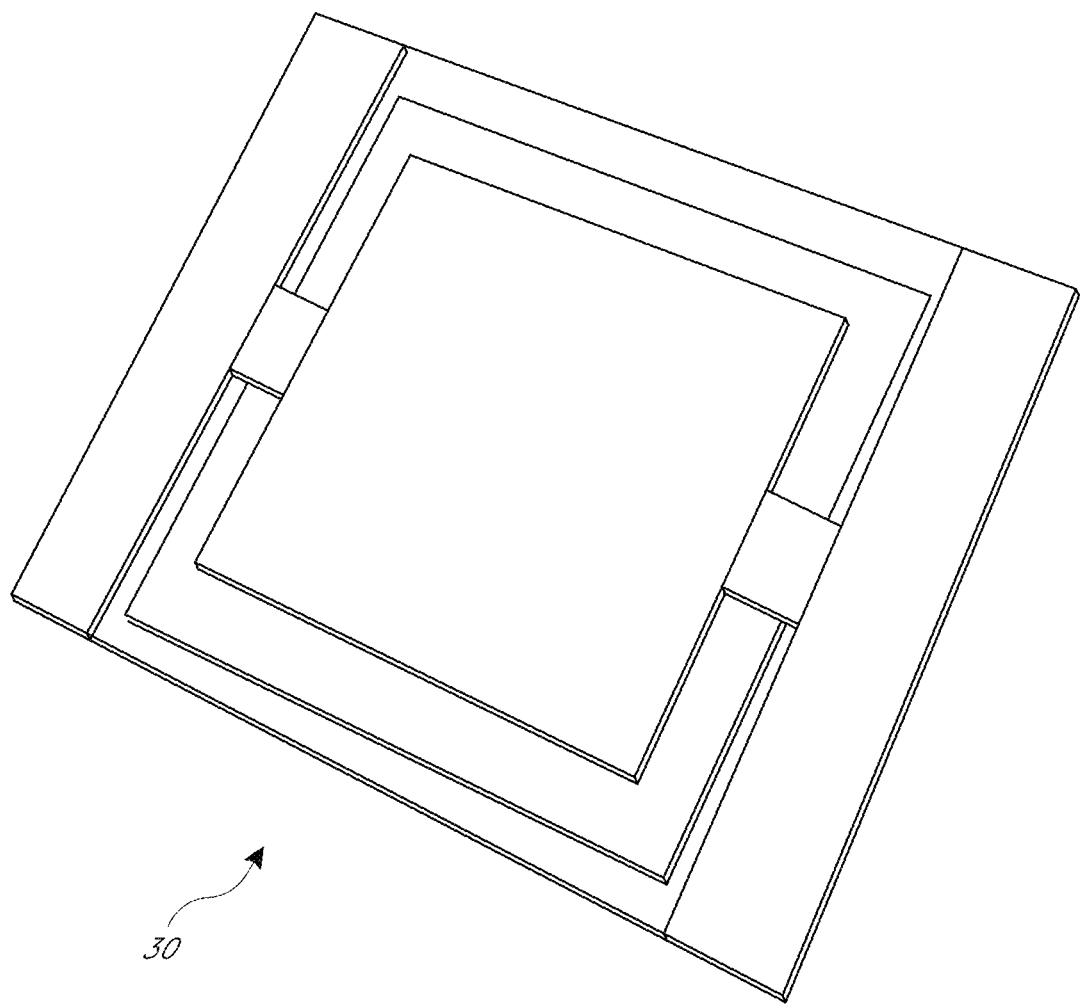
FIG. 4 is a photographic perspective view of another example embodiment of a printed battery.

FIG. 4 is a photographic perspective view of another example of a printed battery 40. The printed battery 40 shown in FIG. 4 is a $Zn/MnO_2$ battery including a polyethylene terephthalate (e.g., Mylar®) substrate and including bus bars for connecting to a potentiostat.

Example Compositions of Printed Battery Layers

An example first electrode layer 2 comprises, by weight:
high molecular weight polyvinylidene difluoride polymer (PVDF, e.g., KYNAR® HSV 900 from Arkema, Inc. of King of Prussia, Pa.)—0.6%
Zn powder (particle size below 10 microns)—99.31%
1 mol/L (M) $ZnBF_4$ in $C_2mimBF_4$ electrolyte—0.09%

An example intermediate layer 3 comprises, by weight:
PVA 133,000 molecular weight—6.86%
PVA 6,000 molecular weight—35.73%
1 M $ZnBF_4$ in $C_2mimBF_4$ electrolyte—57.41%

An example separator layer 4 comprises, by weight:
PVDF (e.g., KYNAR® ADX 161 from Arkema, Inc., of King of Prussia, Pa.)—3.56%
1 M $ZnBF_4$ in $C_2mimBF_4$ electrolyte—36.96%
Glass spheres (less than 20 microns in diameter)—59.48%

An example second electrode layer 5 comprises, by weight:
high molecular weight PVDF HSV 900-4.89%
MWCNT—0.8%
$C_2mimBF_4$ ionic liquid—4.51%
Graphite powder—2.35%
$MnO_2$—87.05%

An example first current collector layer 1 comprises, by weight:
high molecular weight PVDF HSV 900-5.41%
Ni flakes—94.49%

An example second current collector layer 6 comprises, by weight:
high molecular weight PVDF HSV 900-17.42%
Graphene flakes—82.58%

An example insulator layer 7 comprises, by weight:
high molecular weight PVDF HSV 900-100%

Example Printable Ink Compositions (Examples of Successful Ink Compositions), Preparation Process, Properties, and Curing Conditions An example composition of an ink for a first electrode layer 2 comprises, by weight:
high molecular weight PVDF HSV 900-0.51%
Zn powder (particle size below 10 microns)—85.12%
1-methyl-2-pyrrolidinone (MP) solvent—14.29%
1 M $ZnBF_4$ in $C_2mimBF_4$ electrolyte—0.08%

An example procedure to prepare the ink for the first electrode layer 2 includes:
Prepare PVDF HSV 900 base: Heat MP to 60° C. and progressively add PVDF HSV 900. Mix for 30 minutes at 60° C. using a laboratory egg.
Prepare electrolyte: Dissolve $ZnBF_4$ in $C_2mimBF_4$ by mixing at 50° C. in a laboratory egg until the zinc salt is dissolved.
Take PVDF HSV 900 base, electrolyte, and MP and sonicate for 10 minutes.
Take the sonicated mixture, preheat to 40° C., and add additional MP and zinc dust. Stir for 30 minutes using a laboratory egg.

The ink for the first electrode layer 2 fabricated using the example method can have a viscosity of about 10,000 centipoise (cP). An example curing profile for this composition is at a temperature of 130° C. for between 3 and 5 minutes.

An example composition for an ink for an intermediate layer 3 comprises, by weight:
MP solvent—81.19%
PVA 133,000 molecular weight—1.29%
PVA 6,000 molecular weight—6.72%
1 M $ZnBF_4$ in $C_2mimBF_4$ electrolyte—10.8%

An example procedure to prepare the ink for the intermediate layer 3 includes:
Preheat MP to 80° C. Slowly pour PVA 133,000 molecular weight into MP. Mix using magnetic bar.
Add PVA 6,000 molecular weight to the MP solution when the PVA 133,000 is dissolved.
Reduce heat to 60° C. and add $ZnBF_4$ in $C_2mimBF_4$ electrolyte drop wise. Stir using laboratory egg. Cool down the mixture until gelled.

The ink for the intermediate layer 3 fabricated using the example method can have a viscosity of about 100 cP. An example curing profile for this composition is at a temperature of 130° C. for between 5 and 7 minutes.

An example composition of an ink for the separator layer 4 comprises, by weight:
PVDF ADX 161-2.92%
1 M $ZnBF_4$ in $C_2mimBF_4$ electrolyte—30.34%
Glass spheres (less than 20 microns in diameter)—48.82%
MP solvent—17.92%

An example procedure to prepare the ink for the printed separator layer 4 includes:
Prepare PVDF ADX 161 base: Preheat MP to 80° C. Add PVDF ADX 161. Mix until PVDF ADX 161 is dissolved using a laboratory egg.
Preheat PVDF ADX 161 base to 60° C. and add $ZnBF_4$ in $C_2mimBF_4$ electrolyte drop by drop while mixing using a laboratory egg.
Cool down the mixture and add glass spheres. Mix for 10 minutes at room temperature using a laboratory egg.

The ink for the separator layer 4 fabricated using the example method can have a viscosity of about 13,000 cP. An example curing profile for this composition is at a temperature of 130° C. for between 5 and 7 minutes.

An example composition for an ink for a second electrode layer 5 comprises, by weight: high molecular weight PVDF HSV 900-2.3%
MWCNT—0.38%
$C_2mimBF_4$ ionic liquid—2.13%
MP solvent—52.79%
Graphite powder—1.11%
$MnO_2$—41.1%

An example procedure to prepare the ink for the second electrode layer 5 includes:
Prepare MWCNTs paste in $C_2mimBF_4$: Grind a mixture of 15% of the MWCNTs and 85% of the $C_2mimBF_4$ in a mortar and pestle in glove box for 5 minutes, then grind in automated mortar and pestle for 1 hour.
Prepare PVDF HSV 900base: Heat MP to 60° C. and progressively add PVDF HSV 900. Mix for 30 minutes at 60° C. using a laboratory egg.
Take PVDF HSV 900 base and mix with MWCNT paste under sonication and at 50° C. for 30 minutes. Add graphite powder and $MnO_2$ and mix at 70° C. for 90 minutes using a laboratory egg.

The ink for the second electrode layer 5 fabricated using the example method can have a viscosity of about 9,000 cP. An example curing profile for this composition is at a temperature of 130° C. for between 3 and 5 minutes.

An example composition for an ink for the first current collector layer 1 comprises, by weight: PVDF HSV 900-3.63%
Ni flakes—63.47%
MP solvent—32.9%

An example procedure to prepare the ink for the first current collector layer 1 includes:
Prepare PVDF HSV 900 base: Heat MP to 60° C. and progressively add PVDF HSV 900. Mix for 30 minutes at 60° C. using a laboratory egg. Add Ni flakes to the PVDF HSV 900 base while continuing to stir.

An example curing profile for the ink for the first current collector layer 1 fabricated using the example is at a temperature of 130° C. for between 3 and 5 minutes.

An example composition for an ink for the second current collector layer 6 comprises, by weight: PVDF HSV 900-3.24%
Graphene flakes—15.68%
MP solvent—81.08%

An example procedure to prepare the ink for the second current collector layer 6 includes:
Prepare PVDF HSV 900 base: Heat MP to 60° C. and progressively add PVDF HSV 900. Mix for 30 minutes at 60° C. using a laboratory egg. Disperse graphene flakes in MP using ultrasonic bath (15 minutes). Add the grapheme-MP dispersion to the PVDF HSV 900 base while keeping stirring for another 60 minutes.

An example curing profile for the ink for the second current collector layer 2 fabricated using the above example is at a temperature of 130° C. for between 3 and 5 minutes.

An example composition of a polymer insulator layer comprises, by weight: PVDF HSV 900-10%
MP solvent—90%

A higher percentage of PVDF HSV 900 would result in higher viscosity and a lower percentage of PVDF HSV 900 would result in a lower viscosity, which can affect the thickness of a printed layer. Printed layers are generally desired to be as thin as possible, but still able to perform their intended function, such as acting as an environmental barrier for an insulator layer 7.

An example procedure to prepare the ink for the insulator layer 7 includes:
Heat MP to 60° C. and progressively add PVDF HSV 900. Mix for 30 minutes at 60° C. using a laboratory egg. An example curing profile for the ink for the insulator layer 7 fabricated using the above example is at a temperature of 130° C. for between 3 and 5 minutes Example Printed Battery Physical Parameters
Example Thicknesses of the Printed Layers
The current collector layer 1 may have a thickness in a range from about 2 µm to about 5 µm.
A zinc (Zn) electrode layer (e.g., the first electrode layer 2) may have a thickness in a range from about 20 µm to about 70 µm, for example depending on a material of the substrate 8 and absence or presence of the current collector layer 1.
The intermediate layer 3 may have a thickness in a range from about 1 µm to about 3 µm.
The separator layer 4 may have a thickness in a range from about 10 µm to about 30 µm.
A $MnO_2$ electrode layer (e.g., second electrode layer 5) may have a thickness in a range from about 20 µm to about 60 µm.
The second current collector layer 6 may have a thickness in a range from about 5 µm to about 7 µm.
The insulator layer 7 may have a thickness of about 10 µm.

The total thickness of a fully printed battery including the layers 1-7 may have a thickness in a range from about 70 μm to about 200 μm.

The substrate 8 can have thickness in a range from about 10 μm to about 200 μm, making a maximum thickness of the device about 400 μm. On thin substrates 8 (e.g., substrates 8 having a thickness of about 30 μm to about 60 μm), the total thickness of a fully printed battery including the layers 1-7 can be as thin as about 130 microns.

Physical Characteristics of Printed $Zn/MnO_2$ Battery

An example of printed battery 30 on an Al substrate is shown in FIGS. 3A and 3B. The example printed battery 30 has a round shape (e.g., having a diameter of about 18 mm) and has been cut out from the Al substrate. The overall thickness of the battery 30 (including the Al substrate) is about 200 microns. The example battery 30 has a total weight of about 0.137 grams (g). Approximately ⅔ of the total weight is the weight of the 60 microns thick Al substrate.

Figure 5:
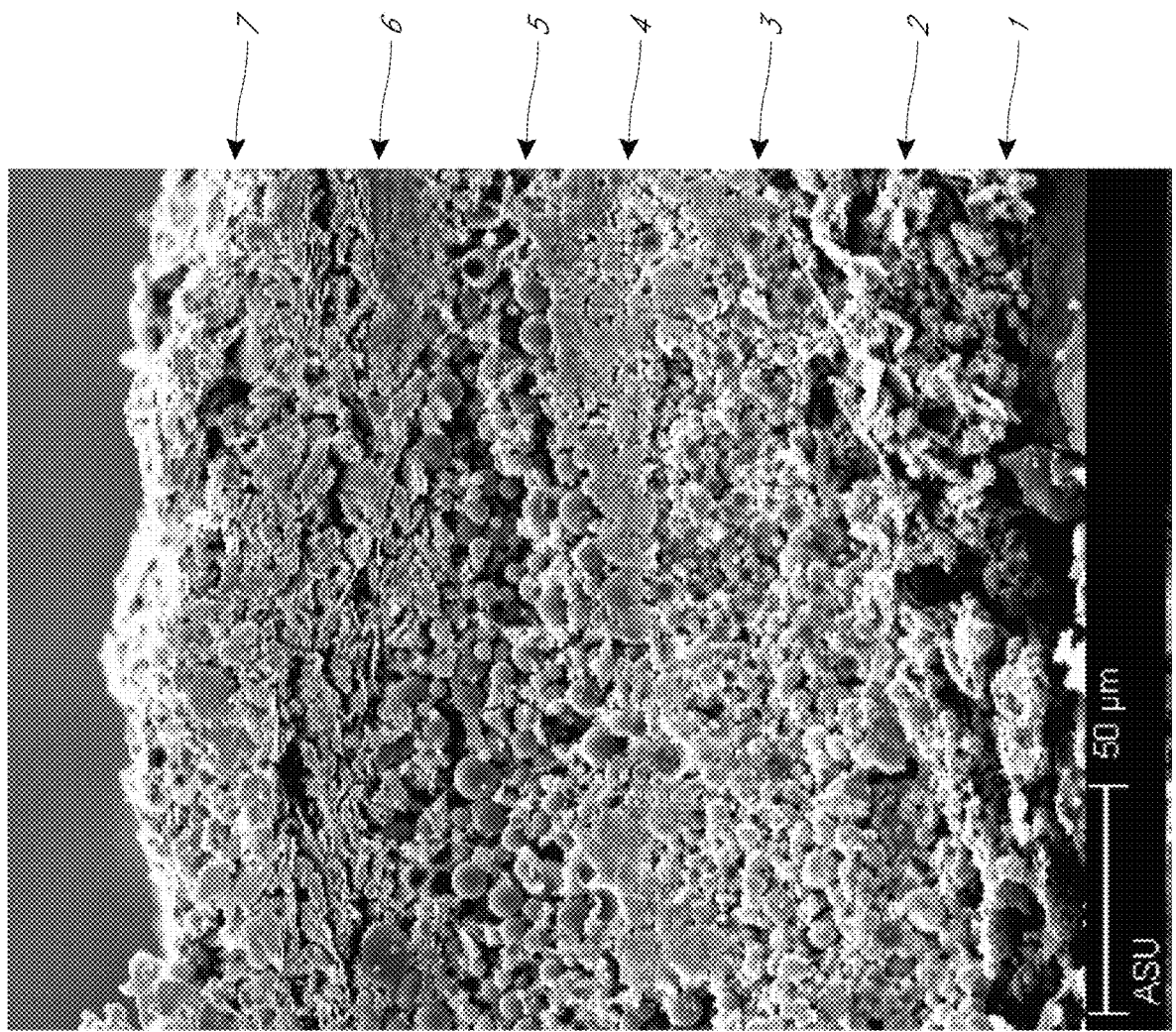
FIG. 5 is a scanning electron microscope (SEM) image of a cross section of an example embodiment of a printed battery.

FIG. 5 shows SEM image of a cross-section of an example printed battery 50. The printed battery 50 shown in FIG. 5 is a $Zn/MnO_2$ battery. The example printed battery was cracked under liquid nitrogen and then imaged. A carbon foam (not shown) was used as a substrate for convenience of the "crack" preparation. The printed $Zn/MnO_2$ battery 50 printed on a carbon foam substrate includes: a carbon foam substrate structure; a thin layer of Ni current collector 1; a Zn anode layer 2 (Zn spheroid particles are visible in FIG. 5); a very thin intermediate layer 3; a glass sphere separator layer 4; a $MnO_2$ layer 5; and a thin graphene current collector layer 6.

Details of the Battery Performance

Figure 6:
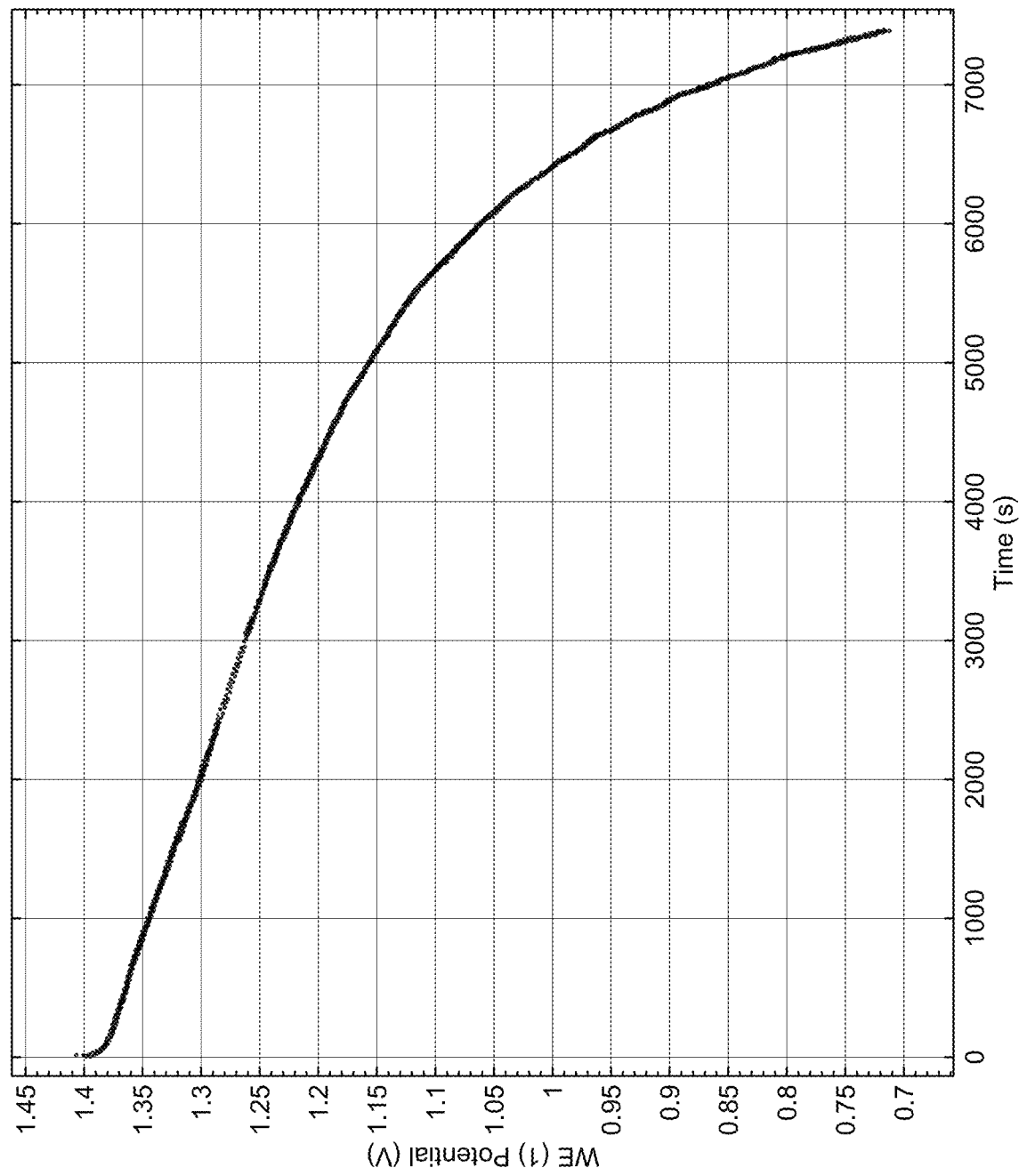
FIG. 6 is a graph of battery potential versus time of discharge for the printed battery of FIGS. 3A and 3B.

FIG. 6 is a graph of the dependence of battery potential versus time of discharge for the printed battery 30 of FIGS. 3A and 3B at constant current of about 0.06 $mA/cm^2$, or a constant current discharge curve. The printed battery 30 was discharged with the current of 0.158 milliAmperes (mA) and lasted 1.9 hours. The cut-off voltage for the calculations was 0.9 V. The capacity of the printed $Zn/MnO_2$ battery 30 is 0.12 $mAh/cm^2$ at moderate current drain of 0.06 $mA/cm^2$. The open circuit potential of the printed battery 30 is 1.5 V and the working voltage is about 1.25 V.

List of Example Alternative Components and Techniques

Polymers

Suitable polymers for one or more layers of the printed battery 10 include, but are not limited to: (or equivalently, polymeric precursors or polymerizable precursors) such as polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and/or chitosan.

In some embodiments, a suitable polymer may be electrostable under a working voltage of a battery. A $Zn/MnO_2$ battery has relatively low voltage, so many polymers may be suitable. For example, fluorinated polymers may be suitable due to their chemical, thermo, and electrochemical stability.

The insulator layer 7 may include a polymer that does not allow penetration by oxygen and/or water into the battery. A variety of PVDF or polyolefins can be used as barrier layer polymers for both water and oxygen. A combination of an oxygen barrier polymer and a moisture barrier polymer from the list above is also possible.

Solvents

Suitable solvents used in preparing one or more inks for fabricating a printed battery include, but are not limited to: water, alcohols such as methanol, ethanol, N-propanol (including 1-propanol, 2-propanol (isopropanol or IPA), 1-methoxy-2-propanol), butanol (including 1-butanol, 2-butanol (isobutanol)), pentanol (including 1-pentanol, 2-pentanol, 3-pentanol), hexanol (including 1-hexanol, 2-hexanol, 3-hexanol), octanol, N-octanol (including 1-octanol, 2-octanol, 3-octanol), tetrahydrofurfuryl alcohol (THFA), cyclohexanol, cyclopentanol, terpineol; lactones such as butyl lactone; ethers such as methyl ethyl ether, diethyl ether, ethyl propyl ether, and polyethers; ketones, including diketones and cyclic ketones, such as cyclohexanone, cyclopentanone, cycloheptanone, cyclooctanone, acetone, benzophenone, acetylacetone, acetophenone, cyclopropanone, isophorone, methyl ethyl ketone; esters such ethyl acetate, dimethyl adipate, proplyene glycol monomethyl ether acetate, dimethyl glutarate, dimethyl succinate, glycerin acetate, carboxylates; carbonates such as propylene carbonate; polyols (or liquid polyols), glycerols and other polymeric polyols or glycols such as glycerin, diol, triol, tetraol, pentaol, ethylene glycols, diethylene glycols, polyethylene glycols, propylene glycols, dipropylene glycols, glycol ethers, glycol ether acetates 1,4-butanediol, 1,2-butanediol, 2,3-butanediol, 1,3-propanediol, 1,4-butanediol, 1,5-pentanediol, 1,8-octanediol, 1,2-propanediol, 1,3-butanediol, 1,2-pentanediol, etohexadiol, p-menthane-3,8-diol, 2-methyl-2,4-pentanediol; tetramethyl urea, n-methylpyrrolidone, acetonitrile, tetrahydrofuran (THF), dimethyl formamide (DMF), N-methyl formamide (NMF), dimethyl sulfoxide (DMSO); thionyl chloride; and/or sulfuryl chloride.

Higher boiling point solvents are generally preferable for printing. A slow evaporation rate can reduce solvent loss during ink mixing and printing, as can influence the shelf life of an ink comprising the solvent.

Ionic Liquids

Ionic liquids (ILs) are generally organic molten salts which consist only of ions and are liquid at temperatures below 100° C. Every ionic liquid has a cation and anion. Suitable ionic liquids can be any combination from the list of cations and the list of anions below. For example, an IL described herein is $C_2mimBF_4$, which is a combination of the first cation and the first anion listed below.

Suitable cations include, but are not limited to: 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, diethylmethylsulfonium, and the like.

Suitable anions include, but are not limited to: tetrafluoroborate, tris(pentafluoroethyl)trifluorophosphate, hexafluorophosphate, ethyl sulfate, dimethyl phosphate, trifluoromethanesulfonate, methansulfonate, triflate, tricyanomethanide, dibutylphosphate, bis(trifluoromethylsulfonyl)imide, bis-2,4,4-(trimethylpentyl) phosphinate, iodide, chloride, bromide, nitrate, and the like.

Zinc Salts

Suitable zinc salts may include, but are not limited to: zinc chloride, zinc bis(trifluoromethanesulfonyl)imide, zinc sulfate, zinc nitrate, and/or zinc carbonate, and the like.

Other examples of suitable zinc salts may include combinations of zinc cation with organic and inorganic anions. In some embodiments, suitable zinc salts have desired solubility in the ionic liquid.

Microspheres

Suitable solid microspheres for the separator layer 4 may be hollow or dense, and may be spherical or substantially spherical particles comprising non-conductive materials like glass, alumina, silica, polystyrene, and/or melamine. The solid microsphere particles size may have a diameter from about 0.5 μm to about 30 μm.

Substrates

Substrates can be conductive and/or non-conductive. Example substrates include, but are not limited to: graphite paper, graphene paper, polyester film, polyimide film, Al foil, copper (Cu) foil, stainless steel (SS) foil, carbon foam, polycarbonate film, paper, coated paper, plastic coated paper, fiber paper, and/or cardboard, and the like.

Printing Techniques

"Printing" includes any and all printing, for example, coating, rolling, spraying, layering, spin coating, laminating and/or affixing processes, for example, screen printing, inkjet printing, electro-optical printing, electroink printing, photoresist and other resist printing, thermal printing, laser jet printing, magnetic printing, pad printing, flexographic printing, hybrid offset lithography, Gravure and other intaglio printing, die slot deposition, and the like.

Ink Preparation Techniques

All kinds of ink mixing techniques are possible, including, but not limited to: mixing with stir bar, mixing with magnetic stirrer, vortexing (Vortex machine), shaking (using shakers), mixing by rotation, sonication, mortar and pestle, and the like.

Curing Conditions

Suitable temperatures for curing an ink used in printing one or more of the battery layers can have a value in a wide temperature range depending on solvents used, for example from about 70° C. to about 300° C. Drying time can vary from about 20 seconds to about 1 hour.

A suitable atmosphere for curing an ink used in printing one or more of the battery layers can be ambient, inert, or vacuum.

EXAMPLE EMBODIMENTS

The following example embodiments identify some possible permutations of combinations of features disclosed herein, although other permutations of combinations of features are also possible.

1. A printed energy storage device comprising:
   a first electrode;
   a second electrode; and
   a separator positioned between the first electrode and the second electrode, at least one of the first electrode, the second electrode, and the separator comprising an ionic liquid,
   wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and
   wherein the ionic liquid includes an anion selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl) phosphinate, iodide, chloride, bromide, and nitrate.

2. The printed energy storage device of Embodiment 1, wherein the ionic liquid comprises 1-ethyl-3-methylimidazolium tetrafluoroborate ($C_2mimBF_4$).

3. The printed energy storage device of Embodiment 1 or 2, wherein the first electrode comprises the ionic liquid.

4. The printed energy storage device of any one of Embodiments 1 to 3, wherein the second electrode comprises the ionic liquid.

5. The printed energy storage device of any one of Embodiments 1 to 4, wherein the separator comprises the ionic liquid.

6. The printed energy storage device of any one of Embodiments 1 to 5, wherein the printed energy storage device further comprises an intermediate layer.

7. The printed energy storage device of Embodiment 6, wherein the intermediate layer is between the first electrode and the separator.

8. The printed energy storage device of Embodiment 6, wherein the intermediate layer is between the second electrode and the separator.

9. The printed energy storage device of any one of Embodiments 6 to 8, wherein the intermediate layer comprises the ionic liquid.

10. The printed energy storage device of any one of Embodiments 1 to 9, wherein the printed energy storage device further comprises a current collector coupled to the first electrode or the second electrode.

11. The printed energy storage device of Embodiment 10, wherein at least one of the first electrode, the second electrode, the separator, the intermediate layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycol-hexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

12. The printed energy storage device of any one of Embodiments 6 to 11, wherein at least one of the first electrode, the intermediate layer, and the separator comprises a salt.

13. The printed energy storage device of Embodiment 12, wherein the salt comprises a zinc salt.

14. The printed energy storage device of Embodiment 12 or 13, wherein the anion of the ionic liquid is the same as an anion of the salt.

15. The printed energy storage device of any one of Embodiments 12 to 14, wherein the salt comprises zinc tetrafluoroborate and the ionic liquid comprises 1-ethyl-3-methylimidazolium tetrafluoroborate.

16. The printed energy storage device of any one of Embodiments 12 to 15, wherein the salt comprises zinc chloride.

17. The printed energy storage device of any one of Embodiments 12 to 16, wherein the salt comprises zinc bis(trifluoromethanesulfonyl)imide.

18. The printed energy storage device of any one of Embodiments 12 to 17, wherein the salt comprises zinc sulfate.

19. The printed energy storage device of any one of Embodiments 12 to 18, wherein the salt comprises zinc nitrate.

20. The printed energy storage device of any one of Embodiments 12 to 19, wherein the salt comprises zinc carbonate.

21. The printed energy storage device of any one of Embodiments 1 to 20, wherein at least one of the first electrode and the second electrode comprises polyvinylidene difluoride.

22. The printed energy storage device of any one of Embodiments 10 to 21, wherein at least one of the second electrode and the current collector comprises carbon nanotubes.

23. The printed energy storage device of Embodiment 22, wherein the carbon nanotubes comprise single-wall carbon nanotubes.

24. The printed energy storage device of Embodiment 22 or 23, wherein the carbon nanotubes comprise multi-wall carbon nanotubes.

25. The printed energy storage device of any one of Embodiments 22 to 24, wherein the second electrode comprises a homogeneous paste comprising the carbon nanotubes and the ionic liquid.

26. The printed energy storage device of any one of Embodiments 1 to 25, wherein the second electrode comprises manganese dioxide.

27. The printed energy storage device of any one of Embodiments 1 to 26, wherein the second electrode comprises a conductive carbon.

28. The printed energy storage device of Embodiment 27, wherein the conductive carbon comprises graphite.

29. The printed energy storage device of any one of Embodiments 10 to 28, wherein the current collector comprises at least one of nickel flakes, graphene flakes, and graphite powder.

30. The printed energy storage device of Embodiment 29, wherein the current collector comprises nickel flakes.

31. The printed energy storage device of Embodiment 29, wherein the current collector comprises graphene flakes.

32. The printed energy storage device of Embodiment 29, wherein the current collector comprises nickel flakes and graphene flakes.

33. The printed energy storage device of Embodiment 29, wherein the current collector comprises nickel flakes, graphene flakes, and graphite powder.

34. The printed energy storage device of Embodiment 29, wherein the current collector comprises nickel flakes and carbon nanotubes.

35. The printed energy storage device of Embodiment 29, wherein the current collector comprises nickel flakes, graphene flakes, and carbon nanotubes.

36. The printed energy storage device of Embodiment 29, wherein the current collector comprises nickel flakes, graphene flakes, carbon nanotubes, and graphite powder.

37. The printed energy storage device of Embodiment 29, wherein the current collector comprises nickel flakes, carbon nanotubes, and graphite powder.

38. The printed energy storage device of any one of Embodiments 10 to 37, wherein the current collector comprises polyvinylidene difluoride.

39. The printed energy storage device of any one of Embodiments 1 to 38, wherein the separator comprises microspheres.

40. The printed energy storage device of Embodiment 39, wherein the microspheres comprises at least one of glass, alumina, silica, polystyrene, and melamine.

41. The printed energy storage device of Embodiment 39 or 40, wherein one or more of the microspheres are hollow.

42. The printed energy storage device of any one of Embodiment 39 or 40, wherein one or more of the microspheres are solid.

43. The printed energy storage device of any one of Embodiments 39 to 42, wherein one or more of the microspheres have a diameter from about 0.5 microns to about 30 microns.

44. The printed energy storage device of any one of Embodiments 1 to 43, wherein the separator comprises polyvinylidene difluoride.

45. The printed energy storage device of any one of Embodiments 6 to 44, wherein the intermediate layer comprises polyvinyl alcohol.

46. The printed energy storage device of any one of Embodiments 1 to 45, wherein the printed energy storage device is a printed zinc-manganese dioxide battery.

47. A layer of a printed energy storage device, the layer comprising
 a salt including an anion; and
 an ionic liquid including the anion.

48. The layer of Embodiment 47, wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium.

49. The layer of Embodiment 47 or 48, wherein the anion is selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl)phosphinate, iodide, chloride, bromide, and nitrate.

50. The layer of any one of Embodiments 47 to 49, wherein the ionic liquid comprises 1-ethyl-3-methylimidazolium tetrafluoroborate (C2mimBF4).

51. The layer of any one of Embodiments 47 to 50, wherein the salt comprises a zinc salt.

52. The layer of any one of Embodiments 47 to 51, wherein the salt comprises zinc tetrafluoroborate.

53. The layer of any one of Embodiments 47 to 52, wherein the salt comprises zinc chloride.

54. The layer of any one of Embodiments 47 to 53, wherein the salt comprises zinc bis(trifluoromethanesulfonyl)imide.

55. The layer of any one of Embodiments 47 to 54, wherein the salt comprises zinc sulfate.

56. The layer of any one of Embodiments 47 to 55, wherein the salt comprises zinc nitrate.

57. The layer of any one of Embodiments 47 to 56, wherein the salt comprises zinc carbonate.

58. The layer of any one of Embodiments 47 to 57, wherein the printed energy storage device comprises a first electrode, a second electrode, and a separator between the first electrode and the second electrode.

59. The layer of any one of Embodiments 47 to 58, wherein the printed energy storage device comprises an intermediate layer.

60. The layer of Embodiment 59, wherein the intermediate layer is between the first electrode and the separator.

61. The layer of Embodiment 59, wherein the intermediate layer is between the second electrode and the separator.

62. The layer of any one of Embodiments 47 to 61, wherein the printed energy storage device further comprises a current collector electrically coupled to the first electrode or the second electrode.

63. The layer of any one of Embodiments 58 to 62, wherein the layer is the first electrode.

64. The layer of any one of Embodiments 58 to 62, wherein the layer is the separator.

65. The layer of any one of Embodiments 59 to 62, wherein the layer is the intermediate layer.

66. The layer of any one of Embodiments 62 to 64, wherein at least one of the first electrode, the second electrode, the separator, the intermediate layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycol-hexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

67. The layer of any one of Embodiments 62 to 66, wherein at least one of the first electrode, the second electrode, the separator, and the current collector comprises polyvinylidene difluoride.

68. The layer of any one of Embodiments 62 to 67, wherein at least one of the second electrode and the current collector comprises carbon nanotubes 69. The layer of Embodiment 68, wherein the carbon nanotubes comprise single-wall carbon nanotubes.

70. The layer of Embodiment 68 or 69, wherein the carbon nanotubes comprise multi-wall carbon nanotubes.

71. The layer of any one of Embodiments 68 to 70, wherein the second electrode comprises a mixture of the carbon nanotubes and the ionic liquid.

72. The layer of any one of Embodiments 58 to 71, wherein the second electrode comprises manganese dioxide.

73. The layer of any one of Embodiments 58 to 72, wherein the second electrode comprises a conductive carbon.

74. The layer of Embodiment 73, wherein the conductive carbon comprises graphite.

75. The layer of any one of Embodiments 62 to 74, wherein the current collector further comprises at least one of nickel flakes, graphene flakes, and graphite powder.

76. The layer of Embodiment 75, wherein the current collector comprises nickel flakes.

77. The layer of Embodiment 76, wherein the current collector is electrically coupled to the first electrode.

78. The layer of Embodiment 75, wherein the current collector comprises graphene flakes.

79. The layer of Embodiment 75, wherein the current collector is electrically coupled to the second electrode.

80. The layer of Embodiment 75, wherein the current collector comprises nickel flakes and graphene flakes.

81. The layer of Embodiment 75, wherein the current collector comprises nickel flakes, graphene flakes, and graphite powder.

82. The layer of Embodiment 75, wherein the current collector comprises nickel flakes and carbon nanotubes.

83. The layer of Embodiment 75, wherein the current collector comprises nickel flakes, graphene flakes, and carbon nanotubes.

84. The layer of Embodiment 75, wherein the current collector comprises nickel flakes, graphene flakes, carbon nanotubes, and graphite powder.

85. The layer of Embodiment 75, wherein the current collector comprises nickel flakes, carbon nanotubes, and graphite powder.

86. The layer of any one of Embodiments 58 to 85, wherein the separator comprises microspheres.

87. The layer of Embodiment 86, wherein the microspheres comprises at least one of glass, alumina, silica, polystyrene, and melamine.

88. The layer of Embodiment 86 or 87, wherein one or more of the microspheres are hollow.

89. The layer of any one of Embodiments 86 or 87, wherein one or more of the microspheres are solid.

90. The layer of any one of Embodiments 86 to 89, wherein one or more of the microspheres have a diameter from about 0.5 microns to about 30 microns.

91. The layer of any one of Embodiments 59 to 90, wherein the intermediate layer comprises polyvinyl alcohol.

92. The layer of any one of Embodiments 47 to 90, wherein the printed energy storage device is a printed zinc-manganese dioxide battery.

93. A layer of a printed energy storage device, the layer comprising:
a salt comprising zinc tetrafluoroborate; and
an ionic liquid comprising 1-ethyl-3-methylimidazolium tetrafluoroborate.

94. The layer Embodiment 93, wherein the printed energy storage device comprises a first electrode, a second electrode, and a separator between the first electrode and the second electrode.

95. The layer of Embodiments 93 or 94, wherein the printed energy storage device comprises an intermediate layer.

96. The layer of Embodiment 95, wherein the intermediate layer is between the first electrode and the separator.

97. The layer of Embodiment 95, wherein the intermediate layer is between the second electrode and the separator.

98. The layer of any one of Embodiments 93 to 97, wherein the printed energy storage device further comprises a current collector coupled to the first electrode or the second electrode.

99. The layer of any one of Embodiments 93 to 98, wherein the layer is the first electrode.

100. The layer of any one of Embodiments 93 to 99, wherein the layer is the separator.

101. The layer of any one of Embodiments 93 to 100, wherein the layer is the intermediate layer.

102. The layer of any one of Embodiments 98 to 101, wherein at least one of the first electrode, the second electrode, the separator, the intermediate layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycol-hexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

103. The layer of any one of Embodiments 98 to 102, wherein at least one of the first electrode, the second electrode, the separator, and the current collector comprises polyvinylidene difluoride.

104. The layer of any one of Embodiments 98 to 103, wherein at least one of the second electrode and the current collector comprises carbon nanotubes.

105. The layer of Embodiment 104, wherein the carbon nanotubes comprise single-wall carbon nanotubes.

106. The layer of Embodiment 104 or 105, wherein the carbon nanotubes comprise multi-wall carbon nanotubes.

107. The layer of any one of Embodiments 104 to 106, wherein the second electrode comprises a homogeneous paste comprising the carbon nanotubes and the ionic liquid.

108. The layer of any one of Embodiments 94 to 107, wherein the second electrode comprises manganese dioxide.

109. The layer of any one of Embodiments 94 to 108, wherein the second electrode comprises a conductive carbon.

110. The layer of Embodiment 109, wherein the conductive carbon comprises graphite.

111. The layer of any one of Embodiments 98 to 110, wherein the current collector further comprises at least one of nickel flakes, graphene flakes, and graphite powder.

112. The layer of Embodiment 111, wherein the current collector comprises nickel flakes.

113. The layer of Embodiment 112, wherein the current collector is coupled to the first electrode.

114. The layer of Embodiment 111, wherein the current collector comprises graphene flakes.

115. The layer of Embodiment 114, wherein the current collector is coupled to the second electrode.

116. The layer of Embodiment 111, wherein the current collector comprises nickel flakes and graphene flakes.

117. The layer of Embodiment 111, wherein the current collector comprises nickel flakes, graphene flakes, and graphite powder.

118. The layer of Embodiment 111, wherein the current collector comprises nickel flakes and carbon nanotubes.

119. The layer of Embodiment 111, wherein the current collector comprises nickel flakes, graphene flakes, and carbon nanotubes.

120. The layer of Embodiment 111, wherein the current collector comprises nickel flakes, graphene flakes, carbon nanotubes, and graphite powder.

121. The layer of Embodiment 111, wherein the current collector comprises nickel flakes, carbon nanotubes, and graphite powder.

122. The layer of any one of Embodiments 94 to 121, wherein the separator comprises microspheres.

123. The layer of Embodiment 122, wherein the microspheres comprises at least one of glass, alumina, silica, polystyrene, and melamine.

124. The layer of Embodiment 122 or 123, wherein one or more of the microspheres are hollow.

125. The layer of any one of Embodiments 122 or 123, wherein one or more of the microspheres are solid.

126. The layer of any one of Embodiments 122 to 125, wherein one or more of the microspheres have a diameter from about 0.5 microns to about 30 microns.

127. The layer of any one of Embodiments 95 to 126, wherein the intermediate layer comprises polyvinyl alcohol.

128. The layer of any one of Embodiments 93 to 127, wherein the printed energy storage device is a printed zinc-manganese dioxide battery.

129. A planarization adhesion layer of a printed energy storage device, the planarization adhesion layer comprising:
polyvinyl alcohol;
a salt; and
an ionic liquid,
wherein the ionic liquid comprises a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and
wherein the ionic liquid comprises an anion selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl) phosphinate, iodide, chloride, bromide, and nitrate.

130. The planarization adhesion layer of Embodiment 129, wherein the salt comprises an anion that is the same as the anion of the ionic liquid.

131. The planarization adhesion layer of Embodiment 129 or 130, wherein the salt comprises a zinc salt.

132. The planarization adhesion layer of any one of Embodiments 129 to 131, wherein the salt comprises zinc tetrafluorborate and the ionic liquid comprises 1-ethyl-3-methylimidazolium tetrafluoroborate.

133. The planarization adhesion layer of any one of Embodiments 129 to 132, wherein the salt comprises zinc chloride.

134. The planarization adhesion layer of any one of Embodiments 129 to 133, wherein the zinc salt comprises zinc bis(trifluoromethanesulfonyl)imide.

135. The planarization adhesion layer of any one of Embodiments 129 to 134, wherein the zinc salt comprises zinc sulfate.

136. The planarization adhesion layer of any one of Embodiments 129 to 135, wherein the zinc salt comprises zinc nitrate.

137. The planarization adhesion layer of any one of Embodiments 129 to 136, wherein the zinc salt comprises zinc carbonate.

138. The planarization adhesion layer of any one of Embodiments 129 to 137, wherein the printed energy storage device comprises a first electrode, a second electrode, and a separator between the first electrode and the second electrode.

139. The planarization adhesion layer of Embodiment 129 to 138, wherein the planarization adhesion layer is between the first electrode and the separator.

140. The planarization adhesion layer of Embodiment 129 to 138, wherein the planarization adhesion layer is between the second electrode and the separator.

141. The planarization adhesion layer of any one of Embodiments 129 to 140, wherein the printed energy storage device further comprises a current collector electrically coupled to the first electrode or the second electrode.

142. The planarization adhesion layer of any one of Embodiments 141, wherein at least one of the first electrode, the second electrode, the separator, the planarization adhesion layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polythelene, polypropylene, polyethylene oxide, polypropylene oxide, polyethylene glycolhexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

143. The planarization adhesion layer of any one of Embodiments 141 or 142, wherein at least one of the first electrode, the second electrode, the separator, and the current collector comprises polyvinylidene difluoride.

144. The planarization adhesion layer of any one of Embodiments 141 to 143, wherein at least one of the second electrode and the current collector comprises carbon nanotubes.

145. The planarization adhesion layer of Embodiment 144, wherein the carbon nanotubes comprise single-wall carbon nanotubes.

146. The planarization adhesion layer of Embodiment 144 or 145, wherein the carbon nanotubes comprise multi-wall carbon nanotubes.

147. The planarization adhesion layer of any one of Embodiments 138 to 146, wherein the second electrode comprises a mixture comprising the carbon nanotubes and the ionic liquid.

148. The planarization adhesion layer of any one of Embodiments 138 to 147, wherein the second electrode comprises manganese dioxide.

149. The planarization adhesion layer of any one of Embodiments 138 to 148, wherein the second electrode comprises a conductive carbon.

150. The planarization adhesion layer of Embodiment 149, wherein the conductive carbon comprises graphite.

151. The planarization adhesion layer of any one of Embodiments 141 to 150, wherein the current collector further comprises at least one of nickel flakes, graphene flakes, and graphite powder.

152. The planarization adhesion layer of Embodiment 151, wherein the current collector comprises nickel flakes.

153. The planarization adhesion layer of Embodiment 152, wherein the current collector is electrically coupled to the first electrode.

154. The planarization adhesion layer of Embodiment 151, wherein the current collector comprises graphene flakes.

155. The planarization adhesion layer of Embodiment 154, wherein the current collector is electrically coupled to the second electrode.

156. The planarization adhesion layer of Embodiment 151, wherein the current collector comprises nickel flakes and graphene flakes.

157. The planarization adhesion layer of Embodiment 151, wherein the current collector comprises nickel flakes, graphene flakes, and graphite powder.

158. The planarization adhesion layer of Embodiment 151, wherein the current collector comprises nickel flakes and carbon nanotubes.

159. The planarization adhesion layer of Embodiment 151, wherein the current collector comprises nickel flakes, graphene flakes, and carbon nanotubes.

160. The planarization adhesion layer of Embodiment 151, wherein the current collector comprises nickel flakes, graphene flakes, carbon nanotubes, and graphite powder.

161. The planarization adhesion layer of Embodiment 151, wherein the current collector comprises nickel flakes, carbon nanotubes, and graphite powder.

162. The planarization adhesion layer of any one of Embodiments 138 to 161, wherein the separator comprises microspheres.

163. The planarization adhesion layer of Embodiment 162, wherein the microspheres comprises at least one of glass, alumina, silica, polystyrene, and melamine.

164. The planarization adhesion layer of Embodiment 162 or 163, wherein one or more of the microspheres are hollow.

165. The planarization adhesion layer of any one of Embodiments 162 or 163, wherein one or more of the microspheres are solid.

166. The planarization adhesion layer of any one of Embodiments 162 to 165, wherein one or more of the microspheres have a diameter from about 0.5 microns to about 30 microns.

167. The planarization adhesion layer of any one of Embodiments 138 to 166, wherein at least one of the first electrode, separator, and second electrode comprises the ionic liquid.

168. The planarization adhesion layer of any one of Embodiments 138 to 167, wherein the printed energy storage device is a printed zinc-manganese dioxide battery.

169. An electrode of a printed energy storage device, the electrode comprising:
carbon nanotubes; and
an ionic liquid,
wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and
wherein the ionic liquid includes an anion selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl) phosphinate, iodide, chloride, bromide, and nitrate.

170. The electrode of Embodiment 169, wherein the carbon nanotubes comprise single-wall carbon nanotubes.

171. The electrode of Embodiment 169 or 170, wherein the carbon nanotubes comprise multi-wall carbon nanotubes.

172. The electrode of any one of Embodiments 169 to 171, wherein the ionic liquid comprises 1-ethyl-3-methylimidazolium tetrafluoroborate.

173. The electrode of any one of Embodiments 169 to 172, wherein the carbon nanotubes are ground.

174. The electrode of any one of Embodiments 169 to 173, wherein the carbon nanotubes and the ionic liquid form a homogeneous mixture.

175. The electrode of any one of Embodiments 169 to 174, wherein the electrode comprises manganese dioxide.

176. The electrode of any one of Embodiments 169 to 175, wherein the electrode comprises graphite powder.

177. The electrode of any one of Embodiments 169 to 176, wherein the printed energy storage device further comprises a second electrode and a separator between the electrode and the second electrode.

178. The electrode of any one of Embodiments 169 to 177, wherein the printed energy storage device further comprises an intermediate layer.

179. The electrode of Embodiment 178, wherein the intermediate layer is between the separator and the electrode.

180. The electrode of Embodiment 178, wherein the intermediate layer is between the separator and the second electrode.

181. The electrode of any one of Embodiments 177 to 180, wherein the printed energy storage device further comprises a current collector electrically coupled to the electrode or the second electrode.

182. The electrode of any one of Embodiments 178 to 181, wherein at least one of the second electrode, the separator, and the intermediate layer comprises the ionic liquid.

183. The electrode of any one of Embodiments 178 to 182, wherein at least one of the second electrode, the separator, and the intermediate layer comprises a salt.

184. The electrode of Embodiment 183, wherein the salt comprises an anion that is the same as an anion of the ionic liquid.

185. The electrode of Embodiment 183 or 184, wherein the salt comprises a zinc salt.

186. The electrode of any one of Embodiments 183 to 185, wherein the salt comprises zinc tetrafluorborate and the ionic liquid comprises 1-ethyl-3-methylimidazolium tetrafluoroborate.

187. The electrode of any one of Embodiments 183 to 186, wherein the salt comprises zinc chloride.

188. The electrode of any one of Embodiments 183 to 188, wherein the salt comprises zinc bis(trifluoromethanesulfonyl)imide.

189. The electrode of any one of Embodiments 183 to 189, wherein the salt comprises zinc sulfate.

190. The electrode of any one of Embodiments 183 to 190, wherein the salt comprises zinc nitrate.

191. The electrode of any one of Embodiments 183 to 191, wherein the salt comprises zinc carbonate.

192. The electrode of any one of Embodiments 181 to 191, wherein at least one of the electrode, the second electrode, the separator, the intermediate layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycol-hexafluoropropylene, polyethylene terefphtalatpolyacrylonitryle, polyvinyl butyral, polyvinyl-caprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

193. The electrode of any one of Embodiments 181 to 192, wherein at least one of the electrode, the second electrode, the separator, and the current collector comprises polyvinylidene difluoride.

194. The electrode of any one of Embodiments 181 to 193, wherein the current collector further comprises at least one of nickel flakes, graphene flakes, and graphite powder.

195. The electrode of Embodiment 194, wherein the current collector comprises nickel flakes.

196. The electrode of Embodiment 195, wherein the current collector is coupled to the second electrode.

197. The electrode of Embodiment 194, wherein the current collector comprises graphene flakes.

198. The electrode of Embodiment 197, wherein the current collector is coupled to the first electrode.

199. The electrode of Embodiment 194, wherein the current collector comprises nickel and graphene flakes.

200. The electrode of Embodiment 194, wherein the current collector comprises nickel flakes, graphene flakes, and graphite powder.

201. The electrode of Embodiment 194, wherein the current collector comprises nickel flakes and carbon nanotubes.

202. The electrode of Embodiment 194, wherein the current collector comprises nickel flakes, graphene flakes, and carbon nanotubes.

203. The electrode of Embodiment 194, wherein the current collector comprises nickel flakes, graphene flakes, carbon nanotubes, and graphite powder.

204. The electrode of Embodiment 194, wherein the current collector comprises nickel flakes, carbon nanotubes, and graphite powder.

205. The electrode of any one of Embodiments 177 to 204, wherein the separator comprises microspheres.

206. The electrode of Embodiment 205, wherein the microspheres comprises at least one of glass, alumina, silica, polystyrene, and melamine.

207. The electrode of Embodiment 205 or 206, wherein one or more of the microspheres are hollow.

208. The electrode of Embodiment 205 or 206, wherein one or more of the microspheres are solid.

209. The electrode of any one of Embodiments 205 to 208, wherein one or more of the microspheres have a diameter from about 0.5 microns to about 30 microns.

210. The electrode of any one of Embodiments 178 to 209, wherein the intermediate layer comprises polyvinyl alcohol.

211. The planarization adhesion layer of any one of Embodiments 169 to 210, wherein the printed energy storage device is a printed zinc-manganese dioxide battery.

212. A printed energy storage device comprising:
a first electrode comprising zinc;
a second electrode comprising manganese dioxide;
a separator between the first electrode and the second electrode; and
a current collector electrically connected to the first electrode or the second electrode, the current collector comprising conductive flakes.

213. The printed energy storage device of Embodiment 212, wherein the current collector further comprises carbon nanotubes.

214. The printed energy storage device of Embodiment 213, wherein the carbon nanotubes comprise single-wall carbon nanotubes.

215. The printed energy storage device of Embodiment 213 or 214, wherein the carbon nanotubes comprise multi-wall carbon nanotubes.

216. The printed energy storage device of any one of Embodiments 212 to 215, wherein the conductive flakes comprise at least one of nickel flakes, graphene flakes, and graphite powder.

217. The printed energy storage device of Embodiment 216, wherein the current collector comprises nickel flakes.

218. The printed energy storage device of Embodiment 217, wherein the current collector is electrically coupled to the first electrode.

219. The printed energy storage device of Embodiment 216, wherein the current collector comprises graphene flakes.

220. The printed energy storage device of Embodiment 219, wherein the current collector is electrically coupled to the second electrode.

221. The printed energy storage device of Embodiment 216, wherein the current collector comprises nickel and graphene flakes.

222. The printed energy storage device Embodiment 216, wherein the current collector comprises nickel flakes, graphene flakes, and graphite powder.

223. The printed energy storage device Embodiment 216, wherein the current collector comprises nickel flakes and carbon nanotubes.

224. The printed energy storage device of Embodiment 216, wherein the current collector comprises nickel flakes, graphene flakes, and carbon nanotubes.

225. The printed energy storage device of Embodiment 216, wherein the current collector comprises nickel flakes, graphene flakes, carbon nanotubes, and graphite powder.

226. The printed energy storage device of any one of Embodiments 212 to 225, wherein the printed energy storage device further includes an intermediate layer.

227. The printed energy storage device Embodiment 226, wherein the intermediate layer is between the first electrode and the separator.

228. The printed energy storage device Embodiment 226, wherein the intermediate layer is between the second electrode and the separator.

229. The printed energy storage device of any one of Embodiment 226 to 228, wherein the at least one of the first electrode, the second electrode, the separator and the intermediate layer comprises an ionic liquid, wherein the ionic liquid includes a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and wherein the ionic liquid includes an anion selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl) phosphinate, iodide, chloride, bromide, and nitrate.

230. The printed energy storage device of Embodiment 240, wherein the ionic liquid comprises 1-ethyl-3-methylimidazolium tetrafluoroborate ($C_2mimBF_4$).

231. The printed energy storage device of any one of Embodiments 226 to 230, wherein at least one of the first electrode, the separator, and the intermediate layer comprises a salt.

232. The printed energy storage device of Embodiment 231, wherein the salt comprises an anion that is the same as the anion of the ionic liquid.

233. The printed energy storage device of any one of Embodiment 231 or 232, wherein the salt comprises zinc tetrafluoroborate and the ionic liquid comprises 1-ethyl-3-methylimidazolium tetrafluoroborate.

234. The printed energy storage device of any one of Embodiments 231 to 233, wherein the salt comprises zinc chloride.

235. The printed energy storage device of any one of Embodiments 231 to 234, wherein the salt comprises zinc bis(trifluoromethanesulfonyl)imide.

236. The printed energy storage device of any one of Embodiments 231 to 235, wherein the salt comprises zinc sulfate.

237. The printed energy storage device of any one of Embodiments 231 to 236, wherein the salt comprises zinc nitrate.

238. The printed energy storage device of any one of Embodiments 231 to 237, wherein the salt comprises zinc carbonate.

239. The printed energy storage device of any one of Embodiments 212 to 250, wherein the first electrode comprises polyvinylidene difluoride.

240. The printed energy storage device of any one of Embodiments 226 to 239, wherein at least one of the first electrode, the second electrode, the separator, the intermediate layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycolhexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organo-modified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

241. The printed energy storage device of any one of Embodiments 213 to 240, wherein the second electrode comprises the carbon nanotubes.

242. The printed energy storage device of Embodiment 241, wherein the second electrode comprises a homogeneous paste comprising the carbon nanotubes and the ionic liquid.

243. The printed energy storage device of any one of Embodiments 212 to 242, wherein the second electrode further comprises a conductive carbon.

244. The printed energy storage device of Embodiment 243, wherein the conductive carbon comprises graphite powder.

245. The printed energy storage device of any one of Embodiments 212 to 244, wherein the separator comprises microspheres.

246. The printed energy storage device of Embodiment 245, wherein the microspheres comprises at least one of glass, alumina, silica, polystyrene, and melamine.

247. The printed energy storage device of Embodiment 245 or 246, wherein one or more of the microspheres are hollow.

248. The printed energy storage device of Embodiment 245 or 246, wherein one or more of the microspheres are solid.

249. The printed energy storage device of any one of Embodiments 245 to 248, wherein one or more of the microspheres have a diameter from about 0.5 microns to about 30 microns.

250. The printed energy storage device of any one of Embodiments 226 to 249, wherein the intermediate layer comprises polyvinyl alcohol.

251. The printed energy storage device of any one of Embodiments 212 to 250, wherein the printed energy storage device is a printed zinc-manganese dioxide battery.

252. A conductive paste for a layer of a printed energy storage device, the conductive paste comprising:
carbon nanotubes; and
an ionic liquid,
wherein the ionic liquid comprises a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-ethyl-3-methylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium, and wherein the ionic liquid comprises an anion selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methansulfonate, triflate, tricyanomethanide, dibutylphosphate, bis(trifluoromethylsulfonyl)imide, bis-2,4,4-(trimethylpentyl) phosphinate, iodide, chloride, bromide, and nitrate.

253. The paste of Embodiment 252, wherein the ionic liquid comprises 1-ethyl-3-methylimidazolium tetrafluoroborate ($C_2mimBF_4$).

254. The paste of Embodiment 252 or 253, wherein the carbon nanotubes are single-wall carbon nanotubes.

255. The paste of Embodiment 252 to 254, wherein the carbon nanotubes are multi-wall carbon nanotubes.

256. The paste of any one of Embodiments 252 to 255, wherein the carbon nanotubes are ground.

257. The paste of any one of Embodiments 252 to 256, wherein the carbon nanotubes and the ionic liquid form a homogeneous mixture.

258. The paste of any one of Embodiments 252 to 257, wherein the layer comprises a first electrode.

259. The paste of Embodiment 258, wherein the first electrode comprises manganese dioxide.

260. The paste of Embodiment 258 or 259, wherein the first electrode comprises graphite.

261. The paste of any one of Embodiments 252 to 260, wherein the printed energy storage device further comprises a second electrode and a separator between the first electrode and the second electrode.

262. The paste of any one of Embodiments 252 to 261, wherein the printed energy storage device further comprises an intermediate layer.

263. The paste of Embodiment 262, wherein the intermediate layer is between the first electrode and the separator.

264. The paste of Embodiment 262, wherein the intermediate layer is between the second electrode and the separator.

265. The paste of any one of Embodiments 252 to 264, wherein the printed energy storage device further comprises a current collector electrically coupled to the first electrode or the second electrode.

266. The paste of any one of Embodiments 262 to 265, wherein at least one of the second electrode, the separator, and the intermediate layer comprises the ionic liquid.

267. The paste of any one of Embodiments 262 to 266, wherein at least one of the second electrode, the separator, and the intermediate layer comprises a salt.

268. The paste of Embodiment 267, wherein the salt comprises a zinc salt.

269. The paste of Embodiment 267 or 268, wherein the salt comprises an anion that is the same as the anion of the ionic liquid.

270. The paste of any one of Embodiments 267 to 269, wherein the salt comprises zinc tetrafluoroborate and the ionic liquid comprises 1-ethyl-3-methylimidazolium tetrafluoroborate.

271. The paste of any one of Embodiments 267 to 270, wherein the salt comprises zinc chloride.

272. The paste of any one of Embodiments 267 to 271, wherein the salt comprises zinc bis(trifluoromethanesulfonyl)imide.

273. The paste of any one of Embodiments 267 to 272, wherein the salt comprises zinc sulfate.

274. The paste of any one of Embodiments 267 to 273, wherein the salt comprises zinc nitrate.

275. The paste of any one of Embodiments 267 to 274, wherein the salt comprises zinc carbonate.

276. The paste of any one of Embodiments 265 to 275, wherein at least one of the first electrode, the second electrode, the separator, the intermediate layer, and the current collector comprises a polymer selected from the group consisting of polyvinyl pyrrolidone (PVP), polyvinyl alcohol (PVA), polyvinylidene fluoride, polyvinylidene fluoride-trifluoroethylene, polytetrafluoroethylene, polydimethylsiloxane, polyethelene, polypropylene, polyethylene oxide, polypropylene oxide, polyethylene glycol-hexafluoropropylene, polyethylene terefphtalatpolyacrylonitryle, polyvinyl butyral, polyvinylcaprolactam, polyvinyl chloride; polyimide polymers and copolymers (including aliphatic, aromatic and semi-aromatic polyimides), polyamides, polyacrylamide, acrylate and (meth)acrylate polymers and copolymers such as polymethylmethacrylate, polyacrylonitrile, acrylonitrile butadiene styrene, allylmethacrylate, polystyrene, polybutadiene, polybutylene terephthalate, polycarbonate, polychloroprene, polyethersulfone, nylon, styrene-acrylonitrile resin; polyethylene glycols, clays such as hectorite clays, garamite clays, organomodified clays; saccharides and polysaccharides such as guar gum, xanthan gum, starch, butyl rubber, agarose, pectin; celluloses and modified celluloses such as hydroxyl methylcellulose, methylcellulose, ethyl cellulose, propyl methylcellulose, methoxy cellulose, methoxy methylcellulose, methoxy propyl methylcellulose, hydroxy propyl methylcellulose, carboxy methylcellulose, hydroxy ethylcellulose, ethyl hydroxyl ethylcellulose, cellulose ether, cellulose ethyl ether, and chitosan.

277. The paste of any one of Embodiments 265 to 276, wherein at least one of the first electrode, the second electrode, the separator, and the current collector comprises polyvinylidene difluoride.

278. The paste of any one of Embodiments 265 to 277, wherein the current collector comprises the carbon nanotubes.

279. The paste of any one of Embodiments 265 to 278, wherein the current collector further comprises at least one of nickel flakes, graphene flakes, and graphite powder.

280. The paste of Embodiment 279, wherein the current collector comprises nickel flakes.

281. The paste of Embodiment 280, wherein the current collector is electrically coupled to the second electrode.

282. The paste of Embodiment 279, wherein the current collector comprises graphene flakes.

283. The paste of Embodiment 282, wherein the current collector is electrically coupled to the first electrode.

284. The paste of Embodiment 279, wherein the current collector comprises nickel and graphene flakes.

285. The paste of Embodiment 279, wherein the current collector comprises nickel flakes, graphene flakes, and graphite powder.

286. The paste of Embodiment 279, wherein the current collector comprises nickel flakes and carbon nanotubes.

287. paste of Embodiment 279, wherein the current collector comprises nickel flakes, graphene flakes, and carbon nanotubes.

288. The paste of Embodiment 279, wherein the current collector comprises nickel flakes, graphene flakes, carbon nanotubes, and graphite powder.

289. The paste of Embodiment 279, wherein the current collector comprises nickel flakes, carbon nanotubes, and graphite powder.

290. The paste of any one of Embodiments 261 to 289, wherein the separator comprises microspheres.

291. The paste of Embodiment 290, wherein the microspheres comprises at least one of glass, alumina, silica, polystyrene, and melamine.

292. The paste of Embodiment 290 or 291, wherein one or more of the microspheres are hollow.

293. The paste of Embodiment 290 or 291, wherein one or more of the microspheres are solid.

294. The paste of any one of Embodiments 290 to 293, wherein one or more of the microspheres have a diameter from about 0.5 microns to about 30 microns.

295. The paste of any one of Embodiments 262 to 294, wherein the intermediate layer comprises polyvinyl alcohol.

296. The paste of any one of Embodiments 252 to 295, wherein the printed energy storage device is a printed zinc-manganese dioxide battery.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Thus, it is intended that the scope of the invention herein disclosed should not be limited by the particular embodiments described above.

The headings provided herein, if any, are for convenience only and do not necessarily affect the scope or meaning of the devices and methods disclosed herein.

What is claimed is:

1. A printed energy storage device comprising:
   a first electrode;
   a printed second electrode comprising a homogeneous paste comprising carbon nanotubes and an ionic liquid; and
   a separator positioned between the first electrode and the second electrode.

2. The printed energy storage device of claim 1, wherein the first electrode comprises zinc.

3. The printed energy storage device of claim 2, wherein the second electrode further comprises manganese dioxide.

4. The printed energy storage device of claim 1, wherein the carbon nanotubes comprise single-wall carbon nanotubes.

5. The printed energy storage device of claim 1, wherein the carbon nanotubes comprise multi-wall carbon nanotubes.

6. The printed energy storage device of claim 1, wherein the ionic liquid comprises:
   a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium; and
   an anion selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methanesulfonate, triflate, tricyanomethanide, dibutylphosphate, bis(trifluoromethylsulfonyl)imide, bis-2,4,4-(trimethylpentyl) phosphinate, iodide, chloride, bromide, and nitrate.

7. The printed energy storage device of claim 6, wherein the ionic liquid comprises 1-ethyl-3-methylimidazolium tetrafluoroborate (C2mimBF4).

8. The printed energy storage device of claim 1, wherein the ionic liquid comprises an organic molten salt that is a liquid at temperatures below 100° C.

9. The printed energy storage device of claim 8, wherein at least one of the first electrode, the second electrode, or the separator comprises a salt different than the organic molten salt.

10. The printed energy storage device of claim 9, wherein the salt comprises zinc.

11. The printed energy storage device of claim 9, wherein the salt comprises an anion that is the same as an anion of the ionic liquid.

12. The printed energy storage device of claim 11, wherein the salt comprises zinc tetrafluoroborate.

13. The printed energy storage device of claim 1, wherein each of the first electrode, the second electrode, and the separator is printed such that the printed energy storage device has a total thickness of 0.1 mm to 0.4 mm.

14. A printed energy storage device comprising:
   a first electrode comprising zinc;
   a second electrode comprising manganese dioxide; and
   a separator positioned between the first electrode and the second electrode,
   wherein the second electrode is a printed electrode comprising carbon nanotubes dispersed in an ionic liquid.

15. The printed energy storage device of claim 14, wherein the carbon nanotubes comprise single-wall carbon nanotubes.

16. The printed energy storage device of claim 14, wherein the carbon nanotubes comprise multi-wall carbon nanotubes.

17. The printed energy storage device of claim 14, wherein the ionic liquid comprises:
   a cation selected from the group consisting of 1-ethyl-3-methylimidazolium, butyltrimethylammonium, 1-butyl-3-methylimidazolium, 1-methyl-3-propylimidazolium, 1-hexyl-3-methylimidazolium, choline, ethylammonium, tributylmethylphosphonium, tributyl(tetradecyl)phosphonium, trihexyl(tetradecyl)phosphonium, 1-ethyl-2,3-methylimidazolium, 1-butyl-1-methylpiperidinium, diethylmethylsulfonium, 1-methyl-3-propylimidazolium, 1-methyl-1-propylpiperidinium, 1-butyl-2-methylpyridinium, 1-butyl-4-methylpyridinium, 1-butyl-1-methylpyrrolidinium, and diethylmethylsulfonium; and
   an anion selected from the group consisting of tetrafluoroborate, tris(pentafluoroethyl)trifluorophosphate, trifluoromethanesulfonate, hexafluorophosphate, tetrafluoroborate, ethyl sulfate, dimethyl phosphate, methanesulfonate, triflate, tricyanomethanide, dibutylphosphate, bis(trifluoromethylsulfonyl)imide, bis-2,4,4-(trimethylpentyl) phosphinate, iodide, chloride, bromide, and nitrate.

18. The printed energy storage device of claim 14, wherein the ionic liquid comprises 1-ethyl-3-methylimidazolium tetrafluoroborate (C2mimBF4).

19. The printed energy storage device of claim 14, wherein the second electrode further comprises a salt having an anion that is the same as an anion of the ionic liquid.

20. The printed energy storage device of claim 14, wherein the second electrode further comprises a salt comprising zinc tetrafluoroborate.

* * * * *

UNITED STATES PATENT AND TRADEMARK OFFICE
CERTIFICATE OF CORRECTION

PATENT NO. : 10,658,679 B2
APPLICATION NO. : 15/986423
DATED : May 19, 2020
INVENTOR(S) : Vera N. Lockett Page 1 of 4

It is certified that error appears in the above-identified patent and that said Letters Patent is hereby corrected as shown below:

On the Title Page

In Column 2, item (57), Abstract, Line 4, delete "second, electrode," and insert --second electrode,--.

On page 2, in Column 2, item (56), U.S. Patent Documents, Line 40, delete "Le" and insert --Lu--.

On page 3, in Column 2, item (56), Other Publications, Line 4, delete "dimentional" and insert --dimensional--.

On page 3, in Column 2, item (56), Other Publications, Line 15, delete "nanostrcutured" and insert --nanostructured--.

On page 3, in Column 2, item (56), Other Publications, Line 16, delete "micro-asseblies" and insert --micro-assemblies--.

On page 3, in Column 2, item (56), Other Publications, Line 55, delete "Enviromental" and insert --Environmental--.

On page 3, in Column 2, item (56), Other Publications, Line 69, delete "Flourine-Doped" and insert --Fluorine-Doped--.

On page 4, in Column 1, item (56), Other Publications, Line 3, delete "Diatomeceous" and insert --Diatomaceous--.

On page 4, in Column 1, item (56), Other Publications, Line 5, delete "Fiatoms" and insert --Diatoms--.

On page 4, in Column 1, item (56), Other Publications, Line 7, delete "micromashinning:" and insert --micromachining:--.

Signed and Sealed this
Twenty-seventh Day of October, 2020

Andrei Iancu
*Director of the United States Patent and Trademark Office*

CERTIFICATE OF CORRECTION (continued)
U.S. Pat. No. 10,658,679 B2

On page 4, in Column 1, item (56), Other Publications, Line 9, delete "Biolofical" and insert --Biological--.

On page 4, in Column 1, item (56), Other Publications, Line 47, delete "poltungstate" and insert --polytungstate--.

On page 4, in Column 2, item (56), Other Publications, Line 11, delete "dimentional" and insert --dimensional--.

On page 4, in Column 2, item (56), Other Publications, Line 39, delete "performancce" and insert --performance--.

On page 4, in Column 2, item (56), Other Publications, Line 54, delete "dimentional" and insert --dimensional--.

In the Specification

In Column 1, Line 44, delete "1.6V" and insert --1.6 V--.

In Column 2, Line 4, delete "methansulfonate," and insert --methanesulfonate,--.

In Column 2, Line 34, delete "polyethelene," and insert --polyethylene,--.

In Column 3, Line 57, delete "methansulfonate," and insert --methanesulfonate,--.

In Column 3, Line 63, delete "(C2mimBF4)." and insert --($C_2$mimBF$_4$).--.

In Column 4, Line 23, delete "polyethelene," and insert --polyethylene,--.

In Column 5, Line 35, delete "polyethelene," and insert --polyethylene,--.

In Column 6, Line 45, delete "methansulfonate," and insert --methanesulfonate,--.

In Column 7, Line 10, delete "polyethelene," and insert --polyethylene,--.

In Column 8, Line 20, delete "methansulfonate," and insert --methanesulfonate,--.

In Column 8, Line 51, delete "(C2mimBF4)" and insert --($C_2$mimBF$_4$)--.

In Column 8, Line 52, delete "tetrafluorborate." and insert --tetrafluoroborate.--.

In Column 8, Line 64, delete "polyethelene," and insert --polyethylene,--.

In Column 10, Line 27, delete "methansulfonate," and insert --methanesulfonate,--.

In Column 10, Line 33, delete "(C2mimBF4)." and insert --($C_2$mimBF$_4$).--.

CERTIFICATE OF CORRECTION (continued)
U.S. Pat. No. 10,658,679 B2

In Column 10, Line 54, delete "polyethelene," and insert --polyethylene,--.

In Column 11, Line 42, delete "methansulfonate," and insert --,--.

In Column 11, Line 47, delete "(C2mimBF4)." and insert --($C_2$mimBF$_4$).--.

In Column 12, Line 20, delete "polyethelene," and insert --polyethylene,--.

In Column 14, Line 25, delete "1.55V" and insert --1.55 V--.

In Column 14, Line 62, delete "the a" and insert --a--.

In Column 16, Line 22, delete "(rpm)" and insert --(μm)--.

In Column 19, Line 57, delete "900base: Heat" and insert --900 base: Heat--.

In Column 21, Line 54, delete "polyethelene," and insert --polyethylene,--.

In Column 22, Line 36, delete "proplyene" and insert --propylene--.

In Column 23, Line 11, delete "methansulfonate," and insert --methanesulfonate,--.

In Column 24, Line 25, delete "methansulfonate," and insert --methanesulfonate,--.

In Column 24, Line 63, delete "polyethelene," and insert --polyethylene,--.

In Column 27, Line 13, delete "methansulfonate," and insert --methanesulfonate,--.

In Column 27, Line 19, delete "(C2mimBF4)." and insert --($C_2$mimBF$_4$).--.

In Column 27, Line 63, delete "polyethelene," and insert --polyethylene,--.

In Column 28, Line 24, delete "nanotubes" and insert --nanotubes.--.

In Column 29, Line 49, delete "polyethelene," and insert --polyethylene,--.

In Column 31, Line 27, delete "methansulfonate," and insert --methanesulfonate,--.

In Column 31, Line 38, delete "tetrafluorborate" and insert --tetrafluoroborate--.

In Column 32, Line 10, delete "polyethelene," and insert --polyethylene,--.

In Column 34, Line 1, delete "methansulfonate," and insert --methanesulfonate,--.

In Column 34, Line 52, delete "tetrafluorborate" and insert --tetrafluoroborate--.

CERTIFICATE OF CORRECTION (continued)
U.S. Pat. No. 10,658,679 B2

In Column 35, Line 6, delete "polyethelene," and insert --polyethylene,--.

In Column 36, Line 47, after "device" insert --of--.

In Column 36, Line 50, after "device" insert --of--.

In Column 36, Line 62, after "device" insert --of--.

In Column 36, Line 65, after "device" insert --of--.

In Column 37, Line 22, delete "methansulfonate," and insert --methanesulfonate,--.

In Column 37, Line 65, delete "polyethelene," and insert --polyethylene,--.

In Column 39, Line 9, delete "methansulfonate," and insert --methanesulfonate,--.

In Column 40, Line 12, delete "polyethelene," and insert --polyethylene,--.

In Column 40, Line 59, delete "paste" and insert --The paste--.

In the Claims

In Column 42, Line 17, Claim 7, delete "(C2mimBF4)." and insert --($C_2mimBF_4$).--.

In Column 43, Line 6, Claim 18, delete "(C2mimBF4)." and insert --($C_2mimBF_4$).--.